(12) United States Patent
Eberhard et al.

(10) Patent No.: US 9,701,741 B2
(45) Date of Patent: Jul. 11, 2017

(54) RBM3 IN BLADDER CANCER

(75) Inventors: Jakob Eberhard, Lund (SE); Karin Jirström, Limhamn (SE)

(73) Assignee: Atlas Antibodies AB, Stockholm (SE)

( * ) Notice: Subject to any disclaimer, the term of this patent is extended or adjusted under 35 U.S.C. 154(b) by 0 days.

(21) Appl. No.: 14/117,704

(22) PCT Filed: May 11, 2012

(86) PCT No.: PCT/EP2012/058826
§ 371 (c)(1),
(2), (4) Date: Feb. 4, 2014

(87) PCT Pub. No.: WO2012/156330
PCT Pub. Date: Nov. 22, 2012

(65) Prior Publication Data
US 2014/0170676 A1    Jun. 19, 2014

Related U.S. Application Data

(60) Provisional application No. 61/487,341, filed on May 18, 2011.

(30) Foreign Application Priority Data

May 18, 2011 (EP) .................... 11166558

(51) Int. Cl.
G01N 33/574 (2006.01)
C07K 16/18 (2006.01)
A61K 31/7068 (2006.01)
A61K 39/395 (2006.01)
A61K 45/06 (2006.01)
C12Q 1/68 (2006.01)
C07K 14/47 (2006.01)
C07K 16/30 (2006.01)

(52) U.S. Cl.
CPC .......... *C07K 16/18* (2013.01); *A61K 31/7068* (2013.01); *A61K 39/39533* (2013.01); *A61K 45/06* (2013.01); *C07K 14/4748* (2013.01); *C07K 16/3038* (2013.01); *C12Q 1/6886* (2013.01); *G01N 33/57407* (2013.01); *G01N 33/57419* (2013.01); *C07K 2317/34* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2004/0076955 A1 * 4/2004 Mack et al. ...................... 435/6

FOREIGN PATENT DOCUMENTS

WO    WO 2010/092190 A2    8/2010

OTHER PUBLICATIONS

Matsui et al (Bioinformatics, 2007, 23:732-738).*
Jogi et al (Modern Pathology, 2009, 22:1564-1574).*
Pilotte et al (Brain Research, 2009, 1258:12-24).*
The Human Protein Atlas, "RBM3," antibody HPA003624, printed Mar. 2016.*
Lipman et al (ILAR Journal, 2005, 46: 259-268).*
Matsui et al., "Genomic characterization of multiple clinical phenotypes of cancer using multivariate linear regression models," Bioinformatics 23:732-738 (2007).
PCT/EP2012/058826 International Preliminary Report on Patentability mailed Apr. 26, 2013.

* cited by examiner

*Primary Examiner* — Laura B Goddard
(74) *Attorney, Agent, or Firm* — Myers Bigel, P.A.

(57) ABSTRACT

The present disclosure relates, in one of its aspects, to a method for determining whether a mammalian subject having a bladder cancer belongs to a first or a second group, wherein the prognosis of subjects of the first group is better than the prognosis of subjects of the second group. The method comprises the steps of: a) evaluating an amount of RBM3 in at least part of a sample earlier obtained from the subject and determining a sample value corresponding to the evaluated amount; b) comparing said sample value with a predetermined reference value; and if said sample value is higher than said reference value, c1) concluding that the subject belongs to the first group; and if said sample value is lower than or equal to said reference value, c2) concluding that the subject belongs to the second group.

5 Claims, 5 Drawing Sheets

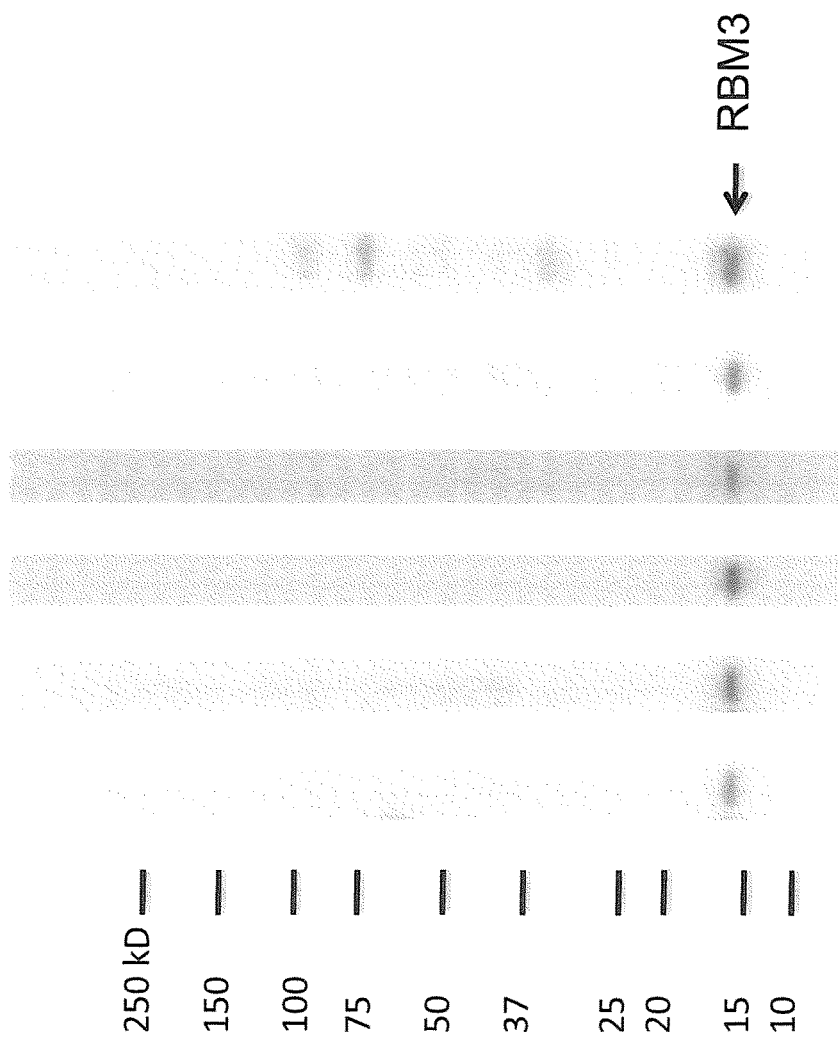

RGFGFITFTNPEHASVAMRAMNGESLDGR (SEQ ID NO: 4)
Peptide 6. CTQRSRGFGFITFTNPEHASV (SEQ ID NO: 23)
Peptide 7. TQRSRGFGFITFTNP (SEQ ID NO: 20)
           GFGFITFTNPEHASV (SEQ ID NO: 24)
           TFTNPEHASVAMRAM (SEQ ID NO: 25)
Peptide 8. TFTNPEHASV (SEQ ID NO: 26)
           FTN (SEQ ID NO: 22)

FIGURE 5

RBM3 IN BLADDER CANCER

RELATED APPLICATIONS

This application is a 35 U.S.C. §371 national phase application of PCT Application PCT/EP2012/058826, filed May 11, 2012, which claims priority to U.S. Provisional Application No. 61/487,341, filed May 18, 2011, and EP 11166558.4, filed May 18, 2011. The entire content of each of these applications is incorporated herein by reference.

TECHNICAL FIELD

The present disclosure relates to the field of bladder cancer and in particular to prognosis and treatment thereof. Further, it relates to means useful in the establishment of a prognosis or treatment prediction.

BACKGROUND

Cancer

Cancer is one of the most common diseases, and a major cause of death in the western world. In general, incidence rates increase with age for most forms of cancer. As human populations continue to live longer, due to an increase of the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelium and skin, followed by cancers originating from the hematopoetic lineage, e.g., leukemia and lymphoma, neuroectoderm, e.g., malignant gliomas, and soft tissue tumors, e.g., sarcomas.

Cancer Diagnostics and Prognostics

Microscopic evaluation of biopsy material from suspected tumors remains the golden standard for cancer diagnostics. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical (IHC) methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ. Staging of tumors is often based on several forms of examination, including surgical, radiological and histopathological analyses. In addition to staging, for most tumor types there is also a classification system to grade the level of malignancy. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is often crucial for a correct diagnosis and may provide an instrument to predict a prognosis. The diagnostic and prognostic information for a specific tumor is taken into account when an adequate therapeutic strategy for a given cancer patient is determined.

A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoetic, sub-classification of lympoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites adds relevant information. However, most of these analyses still represent basic research and have yet to be evaluated and standardized for the use in clinical medicine.

Bladder Cancer

World wide, bladder cancer is the ninth most common form of cancer. Bladder cancer is more common in men than in women; of a total of approximately 336 000 new cases yearly, about 260 000 occur in men and about 76 000 in women. The incidence varies widely between countries, and also the type of cancer. In the industrialized world, the most common type of bladder cancer is urothelial carcinoma (appr. 90% of cases). In developing countries, squamous cell carcinomas are most common, although this type only contributes to a few percent of bladder cancers in the western world. The world wide incidence of urothelial cancer is approximately 3.3% of all new cancers, and nearly 150 000 deaths per year can be contributed to this disease. The risk of developing bladder cancer increases with age and the median age at diagnosis is 70 years for men and women combined.

Today, the largest known risk factor for bladder cancer is use of tobacco, particularly cigarette smoking. Other risk factors include flue gases from coal combustion and ionizing radiation. Genetic factors that contribute to the disease have as yet not been identified.

Bladder Cancer Diagnostics

Screening of patients for early detection of bladder cancer is generally not recommended today. A few markers have been approved by the FDA for use in urine screening, such as BTA-Stat and NMP22, however, these have not proven to be reliable enough. Blood in the urine is a common first symptom of bladder cancer, but is not always present. Other symptoms may be pain across the pubic bone, frequent urination and stinging, or symptoms similar to an ordinary bladder infection. When a patient presents with symptoms that may indicate bladder cancer, a CT-urography is performed. After the CT-urography, a cystoscopic examination is made in which a flexible tube is introduced into the bladder through the urethra. The tube is bearing a camera and a tool to remove tissue from dubious lesions. If tumor tissue is found, resection of the bladder is performed to remove all traces of tumor, and multiple biopsies are also normally taken from the mucous membrane, in a so called mapping procedure.

The cytological diagnosis of grade 1 tumors may be difficult, and the diagnostic accuracy is only about 50% in these cases today. Confounding factors may include e.g. inflammation.

Treatment of Bladder Cancer

Early detection and surgery with excision of the tumor may be of critical importance for a successful treatment. Superficial tumors can be surgically removed or "shaved off", but for invasive tumors, more radical surgery may be needed, whereby the standard approach today is radical cystectomy/removal of the bladder, with or without chemotherapy. Bladder cancer typically metastasizes to regional lymph nodes, but distant metastases in the lung, skin, liver and bones are not unusual.

At the time of diagnosis, usually a transurethral resection of the bladder (TUR-B) is performed, which may in itself be a curative treatment for non-invasive bladder cancer. However, in cases with a high risk of recurrence, patients may be given chemotherapy or Bacillus Calmette-Guerin (BCG) as instillation treatment. In cases with multifocal tumors or frequent recurrences, intravesical instillation during a longer time period may be considered.

Cancer in situ of the bladder is currently treated by BCG instillation. If the tumor fails to respond to treatment, a cystectomy may be performed where all or part of the bladder is removed.

Muscle-invasive bladder cancer, stage T2-T4a, is currently treated by radical cystectomy and lymph node dissection of the small pelvis. Neoadjuvant chemotherapy can also be considered. According to current protocols in Sweden, adjuvant chemotherapy after cystectomy is only recommended to patients enrolled in controlled clinical trials. For inoperable patients, radiation treatment may be given, possibly in combination with chemotherapy.

Prognostics and Treatment Predictive Factors

Prognostic information can be obtained from tumor grade. Urothelial tumors are divided into five grades according to WHO standards: Papillomas, LMP (low malignant potential), and cancer grade 1-3. This grading is based on histological criteria and cell morphology. In grade 1, the tumor cells are well differentiated and grow mainly organized, in grade 2, the tumor cells are moderately differentiated and have a mainly unorganized structure, and in grade 3, the tumor cells are poorly differentiated.

Urothelial tumors are classified according to the TNM staging system. TIS represents tumor (or cancer) in situ. Cancer in situ of the bladder is a flat, low differentiated tumor (grade 3) that occurs in three different forms:

Primary: TIS without other tumor growth present;
Secondary: TIS discovered during follow-up after treatment of an exophytic tumor; or
Concomitant: TIS with other tumor growth present.

Stage Ta is a non-invasive tumor, and in the T1-stage, the tumor has invaded the lamina propria (the subepithelial connective tissue). In stage T2, the tumor invades muscle, in stage T3, the tumor invades perivesical tissue, and in stage T4, the tumor invades other organs.

Approximately 70% of bladder cancers are either entirely superficial tumors or only invading as far as the lamina propria (stage Ta or T1). Local recurrence of these tumors are common (50-70% recurrence rate), and patients normally need to be followed regularly with cystoscopic examinations to detect any recurrences at an early stage. This is a costly procedure causing great discomfort for the patient. These superficial tumors seldom progress to a more aggressive form, but in about 10-15% of cases they do. Among these tumors, three risk groups have been suggested by the European Association of Urology (EAU), namely:

Low risk tumors: Those that are LMP, or stage Ta and grade 1, or less than 3 cm in size;
Medium risk tumors: stage Ta tumors of grade 1 or 2 more than 3 cm in size; and
High risk tumors: tumors of stage Ta and grade 3, stage T1, or Tis.

The high risk tumors have an increased tendency to progress to more aggressive forms, and patients with high risk tumors will have to be closer monitored than those with low or medium risk tumors.

The least malignant tumors, Ta and T1, are associated with a relatively favorable outcome, and a current five-year survival rate of 90 and 75%, respectively. More invasive tumors have a less favorable prognosis with a five-year survival rate of approximately 60% for stage T2 and 35% for stage T3. Tumors with metastases (N1-4 and/or M1) have an even worse prognosis.

Cisplatin-based chemotherapy has proven to be efficient in advanced bladder cancer, with response rates of approx. 30% for single-agent treatment and more than 50% for combination treatment with other agents. However, long-term survival is currently low, only 10-15% of patients survive up to 5 years, and few molecular markers have proven to be of value in prediction of treatment response.

SUMMARY

The inventors have realized that new biomarkers are needed to advance bladder cancer prognostics and treatment prediction. Today, it is difficult to predict in which patients the tumors will progress, and it is thus important to find ways to predict tumor progression at an early stage, sparing low-risk patients as much discomfort as possible when scheduling follow-up cytoscopic examinations. Also, if high-risk patients could be singled out at an early stage, a more aggressive treatment regimen could be used in these patients.

The following is a non-limiting and itemized listing of embodiments of the present disclosure, presented for the purpose of providing various features and combinations provided by the invention in certain of its aspects.

1. Method for determining whether a mammalian subject having a bladder cancer belongs to a first or a second group, wherein the prognosis of subjects of the first group is better than the prognosis of subjects of the second group, comprising the steps of:
   a) evaluating an amount of RBM3 in at least part of a sample earlier obtained from the subject and determining a sample value corresponding to the evaluated amount;
   b) comparing said sample value with a predetermined reference value; and
      if said sample value is higher than said reference value,
   c1) concluding that the subject belongs to the first group; and
      if said sample value is lower than or equal to said reference value,
   c2) concluding that the subject belongs to the second group.

2. Method for determining a prognosis for a mammalian subject having a bladder cancer, comprising the steps of:
   a) evaluating an amount of RBM3 in at least part of a sample earlier obtained from the subject and determining a sample value corresponding to the evaluated amount;
   b) comparing said sample value with a reference value associated with a reference prognosis; and
      if said sample value is higher than said reference value,
   c1) concluding that the prognosis for said subject is better than said reference prognosis; or
      if said sample value is lower than or equal to said reference value,
   c2) concluding that the prognosis for said subject is worse than or equal to said reference prognosis.

3. Method according to item 1 or 2, wherein the prognosis is a probability of survival, such as overall survival, recurrence free survival or bladder cancer specific survival.

4. Method according to item 3, wherein the probability of survival is a probability of five-year, ten-year or 15-year survival.

5. Method for determining whether a subject having a bladder cancer is not in need of a bladder cancer treatment regimen, comprising the steps of:
   a) evaluating an amount of RBM3 in at least part of a sample earlier obtained from the subject and determining a sample value corresponding to the evaluated amount;
   b) comparing said sample value with a predetermined reference value; and
      if said sample value is higher than said reference value,
   c) concluding that said subject is not in need of the bladder cancer treatment regimen.

6. Non-treatment strategy method for a subject having a bladder cancer, comprising:
   a) evaluating an amount of RBM3 in at least part of a sample earlier obtained from the subject and determining a sample value corresponding to the evaluated amount;
   b) comparing said sample value with a predetermined reference value; and
      if said sample value is higher than said reference value,
   c) refraining from treating said subject with a bladder cancer treatment regimen.

7. Method of treatment of a subject having a bladder cancer, comprising the steps of:
   a) evaluating an amount of RBM3 in at least part of a sample earlier obtained from the subject and determining a sample value corresponding to the evaluated amount;
   b) comparing said sample value with a predetermined reference value; and
      if said sample value is lower than or equal to said reference value,
   c) treating said subject with a bladder cancer treatment regimen.

8. Method according to any one of items 5-7, wherein the bladder cancer treatment regimen comprises radical cystectomy and/or radiation treatment.

9. Method according to any one of items 5-8, wherein the bladder cancer treatment regimen comprises neoadjuvant and/or adjuvant chemotherapy.

10. Method according to any one of items 5-9, wherein the bladder cancer treatment regimen comprises administration of Bacillus Calmette-Guérin (BCG).

11. Method according to any one of the preceding items, wherein the bladder cancer is urothelial cancer.

12. Method according to any one of the preceding items, wherein the bladder cancer is a squamous cell carcinoma.

13. Method according to any one of the preceding items, wherein the bladder cancer is stage Ta or T1.

14. Method according to any one of the preceding items, wherein said sample comprises cells, such as tumor cells, from said subject.

15. Method according to any one of the preceding items, wherein said sample is a bladder tissue sample, such as a bladder tumor tissue sample.

16. Method according to item 14 or 15, wherein the evaluation of step a) is limited to the nuclei of cells of said sample.

17. Method according to item 16, wherein the evaluation of step a) is limited to the nuclei of tumor cells of said sample.

18. Method according to any one of the preceding items, wherein said subject is a human.

19. Method according to any one of the preceding items, wherein said reference value is a value corresponding to a predetermined amount of RBM3 protein in a reference sample.

20. Method according to any one of the preceding items, wherein the sample value is a nuclear fraction of nuclear intensity.

21. Method according to item 20, wherein said reference value is a nuclear fraction of 10-75%.

22. Method according to item 20, wherein said reference value is a weak, moderate or strong nuclear intensity.

23. Method according to any one of the preceding items, wherein step a) comprises:
aI) applying to said sample a quantifiable affinity ligand capable of selective interaction with the RBM3 protein to be evaluated, said application being performed under conditions that enable binding of the affinity ligand to RBM3 protein present in the sample; and
aII) quantifying the affinity ligand bound to said sample to evaluate said amount.

24. Method according to any one of items 1-22, wherein step a) comprises:
a1) applying to said sample a quantifiable affinity ligand capable of selective interaction with the RBM3 protein to be quantified, said application being performed under conditions that enable binding of the affinity ligand to RBM3 protein present in the sample;
a2) removing non-bound affinity ligand; and
a3) quantifying affinity ligand remaining in association with the sample to evaluate said amount.

25. Method according to item 23 or 24, wherein the quantifiable affinity ligand is selected from the group consisting of antibodies, fragments thereof and derivatives thereof.

26. Method according to item 25, wherein said quantifiable affinity ligand is obtainable by a process comprising a step of immunizing an animal with a peptide whose amino acid sequence consists of a sequence selected from SEQ ID NO:4 and 5.

27. Method according to item 25, wherein said quantifiable affinity ligand is obtainable by a process comprising a step of immunizing an animal with an RBM3 fragment which consists of 21 amino acid residues or less, such as 15 amino acid residues or less, and comprises a sequence selected from SEQ ID NO:6-19 and 22-26.

28. Method according to item 25, wherein said quantifiable affinity ligand is obtainable by a process comprising a step of immunizing an animal with an RBM3 fragment which consists of 20 amino acid residues or less, such as 15 amino acid residues or less, such as 10 amino acid residues or less and comprises a sequence selected from SEQ ID NO: 8, 16, 17, 22, 24, 25 and 26.

29. Method according to item 23 or 24, wherein said quantifiable affinity ligand is an oligonucleotide molecule.

30. Method according to item 23 or 24, wherein the quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

31. Method according to any one of items 23-30, wherein said quantifiable affinity ligand is capable of selective interaction with a peptide whose amino acid sequence consists of a sequence SEQ ID NO: 1.

32. Method according to any one of items 23-31, wherein said quantifiable affinity ligand is capable of selective interaction with a peptide consisting of an amino acid sequence selected from SEQ ID NO: 4 and 5.

33. Method according to any one of items 23-32, wherein said quantifiable affinity ligand is capable of selective interaction with an RBM3 fragment which consists of 21 amino acid residues or less, such as 15 amino acid residues or less, and comprises an amino acid sequence selected from SEQ ID NO: 6-19 and 22-26.

34. Method according to any one of items 23-33, wherein said quantifiable affinity ligand is capable of selective interaction with an RBM3 fragment which consists of 20 amino acid residues or less, such as 15 amino acid residues or less, and comprises a sequence selected from SEQ ID NO: 8, 16, 17, 22, 24, 25 and 26.

35. Method according to any one of items 23-34, wherein said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

36. Method according to any one of items 23-35, wherein said quantifiable affinity ligand is detected using a secondary affinity ligand capable of recognizing said quantifiable affinity ligand.

37. Method according to item 36, wherein said secondary affinity ligand capable of recognizing said quantifiable affinity ligand comprises a label selected from the group consisting of fluorescent dyes and metals, chromophoric dyes, chemiluminescent compounds and bioluminescent proteins, enzymes, radioisotopes, particles and quantum dots.

38. Use ex vivo of an RBM3 protein as a prognostic marker for bladder cancer.

39. Use according to item 38, wherein said protein is provided in a sample from a subject having a bladder cancer.

40. Use according to item 39, wherein said sample is a bladder cancer tissue sample.

41. Use according to any one of items 38-40, wherein said marker is a marker of a relatively good prognosis for bladder cancer.

42. Use ex vivo of an RBM3 protein, or an antigenically active fragment thereof, for the selection or purification of a bladder cancer prognostic agent.

43. Use of an RBM3 protein, or an antigenically active fragment thereof, for the production of a bladder cancer prognostic agent.

44. Use according to item 42 or 43, wherein said prognostic agent is an affinity ligand capable of selective interaction with the RBM3 protein or the antigenically active fragment thereof.

45. Use according any one of items 38-44, wherein the amino acid sequence of the RBM3 protein comprises a sequence selected from:
  i) SEQ ID NO: 1; and
  ii) a sequence which is at least 85% identical to SEQ ID NO: 1.

46. Use according any one of items 38-44, wherein the amino acid sequence of the RBM3 protein comprises or consists of a sequence selected from:
  i) SEQ ID NO: 2; and
  ii) a sequence which is at least 85% identical to SEQ ID NO:2.

47. Use of an antigenically active fragment according to any one of items 42-44, wherein the fragment consists of 50 amino acid residues or less and comprises or consists of an amino acid sequence selected from SEQ ID NO: 4-19 and 22-26.

48. Use according to item 47, wherein the fragment consists of 29 amino acid residues or less.

49. Use according to item 48, wherein the fragment consists of 21 amino acid residues or less and comprises an amino acid sequence selected from SEQ ID NO: 6-19 and 22-26.

50. Use according to item 49, wherein the fragment consists of 20 amino acid residues or less and comprises an amino acid sequence selected from SEQ ID NO: 8, 16, 17, 22, 24, 25 and 26.

51. Use according to item 49 or 50, wherein the fragment consists of 15 amino acid residues or less, such as 10 amino acid residues or less.

52. Use ex vivo of an affinity ligand capable of selective interaction with an RBM3 protein as a bladder cancer prognostic agent.

53. Use according to item 52, wherein the affinity ligand is obtainable by a process comprising a step of immunizing an animal with a peptide whose amino acid sequence consists of sequence SEQ ID NO: 4 or 5 or a RBM3 protein fragment which consists of 21 amino acid residues or less, such as 15 amino acid residues or less, such as 10 amino acid residues or less and comprises an amino acid sequence selected from SEQ ID NO: 6-19 and 22-26.

54. Use according to item 52, wherein the affinity ligand is obtainable by a process comprising a step of immunizing an animal with a peptide whose amino acid sequence consists of SEQ ID NO:5 or a RBM3 protein fragment which consists of 20 amino acid residues or less, such as 15 amino acid residues or less, such as 10 amino acid residues or less and comprises a sequence selected from SEQ ID NO: 8, 16, 17, 22, 24, 25 and 26.

55. Use according to item 52, wherein the affinity ligand is capable of selective interaction with a peptide whose amino acid sequence consists of SEQ ID NO:4 or 5 or an RBM3 fragment which consists of 21 amino acid residues or less, such as 15 amino acid residues or less, such as 10 amino acid residues or less and comprises an amino acid sequence selected from SEQ ID NO:6-19 and 22-26.

56. Use according to item 52, wherein the affinity ligand is capable of selective interaction with a peptide whose amino acid sequence consists of SEQ ID NO:5 or an RBM3 fragment which consists of 20 amino acid residues or less, such as 15 amino acid residues or less, such as 10 amino acid residues or less and comprises an amino acid sequence selected from SEQ ID NO: 8, 16, 17, 22, 24, 25 and 26.

57. RBM3 protein fragment, which consists of 21 amino acid residues or less and comprises a sequence selected from SEQ ID NO: 22-26.

58. RBM3 protein fragment according to item 57, which consists of 15 amino acid residues or less, such as 10 amino acid residues residues or less, such as 6 amino acid residues or less.

59. RBM3 protein fragment according to item 57 or 58, which comprises a sequence selected from SEQ ID NO: 22, 24, 25 and 26.

60. Affinity ligand capable of selective interaction with an RBM3 protein fragment consisting of 21 amino acid residues or less and comprising a sequence selected from SEQ ID NO: 22-26.

61. Affinity ligand according to item 60 capable of selective interaction with an RBM3 protein fragment consisting of the amino acid residues of SEQ ID NO: 24 or 25.

62. Affinity ligand according to item 60 capable of selective interaction with an RBM3 protein fragment consisting of 10 amino acid residues or less and comprising a sequence selected from SEQ ID NO: 22 and 26.

63. Affinity ligand according to item 62 capable of selective interaction with an RBM3 protein fragment consisting of 6 amino acid residues or less and comprising the sequence SEQ ID NO: 22.

64. Polyclonal or monoclonal antibody according to any one of items 60-63.

BRIEF DESCRIPTION OF THE FIGURES

FIG. 3 shows the impact of RBM3 expression on overall survival (OS) of patients in cohort II. Patients were divided into two groups based on RBM3 expression. The solid line represents patients with low RBM3 expression, nuclear score (NS)≤1, and the dotted line represents patients with high RBM3 expression (NS>1).

FIG. 4 shows Western blot results for, from left to right, 7F5, 10F1, 12A10, 12C9, 14D9 and anti-RBM3. Thus, lanes 1 through 5 show the monoclonal antibodies while lane 6 shows the polyclonal anti-RBM3 antibody.

FIG. 5 shows alignment of SEQ ID NO:4 as well as the peptides used for epitope mapping of the monoclonal antibodies.

DETAILED DESCRIPTION

Figure 1A:
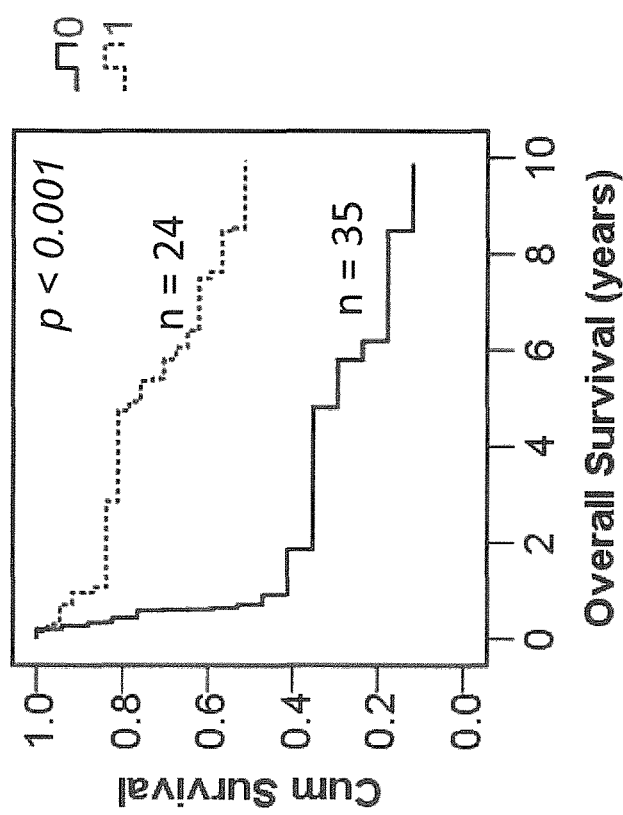
FIG. 1A shows the impact of RBM3 expression on overall survival (OS) of all patients in cohort I, i.e. 59 subjects, diagnosed with urothelial cancer. Patients were divided into two groups based on RBM3 expression. The solid line represents patients with low RBM3 expression, nuclear score (NS)≤3, and the dotted line represents patients with high RBM3 expression (NS>3).

As a first aspect of the present disclosure, there is thus provided a method for determining whether a mammalian subject having a bladder cancer belongs to a first or a second group, wherein the prognosis of subjects of the first group is better than the prognosis of subjects of the second group, comprising the steps of:

a) evaluating an amount of RBM3 in at least part of a sample earlier obtained from the subject and determining a sample value corresponding to the evaluated amount;

b) comparing said sample value with a predetermined reference value; and if said sample value is higher than said reference value, c1) concluding that the subject belongs to the first group; and if said sample value is lower than or equal to said reference value, c2) concluding that the subject belongs to the second group.

The present invention based on an RNA-binding motif 3 (RBM3) level as a bladder cancer status indicator has a number of benefits. As well known by the person skilled in the art, a prognosis may be important for various reasons. Frequently, the prognosis for a bladder cancer subject reflects the aggressiveness of the cancer. In general, identification of the level of aggressiveness of a bladder cancer is of vital importance as it helps a physician selecting an appropriate treatment strategy. For example, if a particularly aggressive form of the cancer is identified, a painful or in any other sense unpleasant treatment, which normally is avoided, may anyway be considered. Further, if less aggressive forms can be identified, over-treatment may be avoided.

Also, in case of a subject having a bladder cancer of an advanced stage, the additional prognostic information provided by the methods of the present disclosure may guide the physician (and the subject) deciding whether to apply an aggressive treatment in hope of prolonged survival or proceed with palliative treatment to relieve the subject from suffering during the remaining time. A high RBM3 level would here be in favor of the former alternative.

In a morphological examination of a sample from a bladder cancer subject, it may be difficult to determine if the tumor has invaded muscular tissue or not. That is, it may be difficult for a pathologist to determine if the tumor is of TNM stage T1 or T2. In such situations, the additional prognostic information obtained by the methods of the present disclosure may be particularly relevant.

In addition, the RBM3 protein, as a marker for which a certain level of expression is correlated with a certain pattern of disease progression, has a great potential for example in a panel for making predictions or prognoses or for the selection of a treatment regimen.

In the method of the first aspect, it is determined whether a bladder cancer subject belongs to a first or a second group, wherein subjects of the first group generally have a better prognosis than subjects of the second group. The division of bladder cancer subjects into the two groups is determined by comparing samples values from the subjects with a reference value. Various reference values may be employed to discriminate between subjects that generally survived for a comparatively long period (represented by the upper curve) and subjects that generally survived for a comparatively short period (represented by the lower curve). The reference value is thus the determinant for the size of the respective groups; the higher the reference value, the fewer the subjects in the first group and the lower the likelihood that a tested subject belongs to the first group. As the prognosis generally decreases as the sample value decreases, a relatively low reference value may in some instances be selected to identify subjects with a particularly poor prognosis. Guided by the present disclosure, the person skilled in the art may select relevant reference values without undue burden.

The first and the second group may consist exclusively of subjects having bladder cancers of the same or similar grade, stage and/or type as the tested subject.

When the first and the second group may consist exclusively of subjects having bladder cancers of the same stage as the tested subject, the prognosis is a stage-independent prognosis. A stage-independent prognosis is particularly interesting as it provides information beyond what is available from the traditional staging.

When the first and the second group may consist exclusively of subjects having bladder cancers of the same grade as the tested subject, the prognosis is a grade-independent prognosis. A grade-independent prognosis is particularly interesting as it provides information beyond what is available from the traditional grading.

Further, the groups may consist only of subjects having the same or similar age, race, sex, genetic characteristics and/or medical status or history.

Consequently, a physician may use the method according to the first aspect to obtain additional information regarding the prognosis of a bladder cancer subject, which in turn may help him to make informed decisions regarding following actions.

The prognosis of the tested subject may also be determined relative to a reference prognosis. Accordingly, as a first configuration of the first aspect, there is provided a method for determining a prognosis for a mammalian subject having a bladder cancer, comprising the steps of:

a) evaluating an amount of RBM3 in at least part of a sample earlier obtained from the subject and determining a sample value corresponding to the evaluated amount;

b) comparing said sample value with a reference value associated with a reference prognosis; and
    if said sample value is higher than said reference value,
c1) concluding that the prognosis for said subject is better than said reference prognosis; or
    if said sample value is lower than or equal to said reference value,
c2) concluding that the prognosis for said subject is worse than or equal to said reference prognosis.

However closely related and covered by the same concept, c1) and c2) provide two alternative conclusions.

Similarly and as a second configuration of the first aspect, there is provided a method for determining whether a prognosis for a mammalian subject having a bladder cancer is better than a reference prognosis, comprising the steps of:

a) evaluating an amount of RBM3 protein present in at least part of a sample earlier obtained from the subject and determining a sample value corresponding to the evaluated amount;

b) comparing the sample value obtained in step a) with a reference value associated with a reference prognosis; and,
    if said sample value is higher than said reference value,
c) concluding that the prognosis for said subject is better than said reference prognosis.

It follows that as a third configuration of the first aspect, there is provided a method for determining whether a prognosis for a mammalian subject having a bladder cancer is worse than or equal to a reference prognosis, comprising the steps of:

a) evaluating an amount of RBM3 present in at least part of a sample earlier obtained from the subject and determining a sample value corresponding to the evaluated amount;

b) comparing the sample value obtained in step a) with a reference value associated with a reference prognosis; and,
    if said sample value is lower than or equal to said reference value,
c) concluding that the prognosis for said subject is worse than or equal to said reference prognosis.

The inventive concept of the present disclosure may also form the basis for a decision to refrain from a certain treatment regimen.

For example, the prognoses for subjects showing high RBM3 levels are generally better than those for subjects showing low RBM3 levels, as shown in the attached figures. Provided with the teachings of the present disclosure, a physician may consider the prognosis of an RBM3 high subject as being so favorable that certain treatment regimens are avoided and a less aggressive treatment regimen is selected instead. Thus, radical cystectomy or radiation therapy may be selected only if the subject is RBM3 low. In other cases, the decision may be to refrain from any adjuvant therapy when the subject is RBM3 high. As another example, mono-therapy may be selected instead of a combination therapy or a therapeutic agent may be given in a lower dose if the subject shows a high RBM3 value.

In conclusion, the present disclosure may relieve subjects from over-treatment.

Thus, as a fourth configuration of the first aspect, there is provided a method for determining whether a subject having a bladder cancer is not in need of a bladder cancer treatment regimen, comprising the steps of:
a) evaluating an amount of RBM3 in at least part of a sample earlier obtained from the subject and determining a sample value corresponding to the evaluated amount;
b) comparing said sample value with a predetermined reference value; and
if said sample value is higher than said reference value,
c) concluding that said subject is not in need of the bladder cancer treatment regimen.

Further, as a fifth configuration of the first aspect, there is provided a non-treatment strategy method for a subject having a bladder cancer, comprising:
a) evaluating an amount of RBM3 in at least part of a sample earlier obtained from the subject and determining a sample value corresponding to the evaluated amount;
b) comparing said sample value with a predetermined reference value; and
if said sample value is higher than said reference value,
c) refraining from treating said subject with a bladder cancer treatment regimen.

For example, step c) of the fifth configuration may be a refraining from the treatment regimen during at least one week from the completion of steps a)-b), such as at least one month from the completion of steps a)-b), such as at least three months from the completion of steps a)-b), such as at least six months from the completion of steps a)-b), such as at least one year from the completion of steps a)-b), such as at least two years from the completion of steps a)-b).

Alternatively, the refraining of step c) may be a refraining from treatment until the next time the method is performed or until a recurrence of a bladder cancer.

As an alternative configuration of the first aspect, there is provided a method for establishing a prognosis for a mammalian subject having a bladder cancer, comprising the steps of:
a) evaluating an amount of RBM3 protein present in at least part of a sample from the subject, and determining a sample value corresponding to the evaluated amount; and
b) correlating the sample value of step a) to the prognosis for the subject.

In the context of the present disclosure, "establishing a prognosis" refers to establishing a specific prognosis or a prognosis interval.

In an embodiment of the alternative configuration, the sample may be an earlier obtained sample.

The correlating of step b) refers to any way of associating survival data to the obtained sample value so as to establish a prognosis for the subject.

In the present disclosure, different RBM3 values (sample values) corresponding to various prognoses are presented. Typically, a low sample value is associated with a poorer prognosis than a high sample value. In the method of the third configuration of the first aspect, the sample value is compared to a reference value, and if the sample value is equal to or lower than the reference value, it is concluded that the prognosis for the subject is equal to, or worse than, a reference prognosis associated with the reference value.

Consequently, the method may be adapted to a reference value. In such case, starting from a sample value which under the circumstances is considered to be relevant, a reference value which is equal to the sample value may be selected. Subsequently, a reference prognosis associated with that reference value may be established. Guided by the present disclosure, the person skilled in the art understands how to establish a reference prognosis which corresponds to a given reference value. For example, the relation between sample values and survival data in a relevant group of cancer patients may be examined in line with what is described in Examples below. The procedure described therein may be adapted to a given reference value. Then, a prognosis corresponding to the given reference value may be selected as the reference prognosis.

Also, the method may be adapted to a given reference prognosis. In such case, starting from a reference prognosis which under the circumstances is considered to be relevant, for example for selecting an appropriate therapy, a corresponding reference value may be established. Guided by the present disclosure, the person skilled in the art understands how to establish a reference value which corresponds to a given reference prognosis. For example, the relation between sample values and survival data in a group of cancer patients may be examined as in Examples below, but the procedure described therein may be adapted to establish reference values corresponding to a given reference prognosis. For example, different reference values may be tested until one which correlates with the given reference prognosis is found.

The reasoning above applies mutatis mutandis to the other configurations of the first aspect.

Accordingly, the reference prognosis of the configurations of the first aspect may be based on a previously established prognosis, e.g., obtained by an examination of a relevant population of subjects. Such reference population may be selected to match the tested subject's age, sex, race, bladder cancer stage, bladder cancer type and/or medical status and history. Further, a prognosis may be adapted to a background risk in the general population, a statistical prognosis/risk or an assumption based on an examination of the subject. Such examination may also comprise the subject's age, sex, race, bladder cancer stage, bladder cancer type and/or medical status and history. Thus, a physician may for example adapt the reference prognosis to the subject's bladder cancer history, the type and/or stage of the tumor, the morphology of the tumor, the location of the tumor, the presence and spread of metastases and/or further cancer characteristics.

In general, when deciding on a suitable treatment strategy for a patient having bladder cancer, the physician responsible for the treatment may take several parameters into account, such as the result of an immunohistochemical evaluation, patient age, tumor type, stage and grade, general condition and medical history, such as bladder cancer history. To be guided in the decision, the physician may perform a RBM3 test, or order a RBM3 test performed, according to the first aspect. Further, the physician may assign to someone else, such as a lab worker, to perform step a), and optionally step b), while performing step c), and optionally b), himself.

The inventive concept of the present disclosure may also form the basis for applying various treatment regimes.

For example, the prognosis for subjects showing low RBM3 protein levels is generally worse than those for subjects showing high RBM3 protein levels, as shown in the attached figures. Provided the teachings of the present disclosure, a physician may thus consider the prognosis of an RBM3 protein low subject as being so poor that a certain treatment regimen is appropriate. The present disclosure may thus provide for accurate treatment of a previously undertreated group.

As a second aspect of the present disclosure, there is thus provided a method of treatment of a subject having a bladder cancer, comprising the steps of:
 a) evaluating an amount of RBM3 in at least part of a sample earlier obtained from the subject and determining a sample value corresponding to the evaluated amount;
 b) comparing said sample value with a predetermined reference value; and
  if said sample value is lower than or equal to said reference value,
 c) treating said subject with a bladder cancer treatment regimen.

According to one embodiment, the method may comprise the additional step:
 d) and if said sample value is higher than said reference value, refraining from treating said subject with the bladder cancer treatment regimen.

In one embodiment of the method of the second aspect, the reference value of step b) may be associated with a reference prognosis and said treatment regimen of step c) may be adapted to a prognosis which is worse than or equal to the reference prognosis. In such an embodiment, the method may comprise the additional step: d) and if said sample value is higher than said reference value, treating said subject with a treatment regimen adapted to a prognosis which is better than the reference prognosis, for which the appropriate treatment regimen may be no treatment.

The physician responsible for the treatment according to the second aspect may assign to someone else, such as a lab worker, to perform step a), and optionally step b), while performing step c), and optionally b), himself.

Further, the results of steps a) and b) may be at hand when the method of treatment according to the second aspect is initiated.

Thus, the method may be applying a bladder cancer treatment regimen to a subject having a bladder cancer when a sample value corresponding to an amount of RBM3 in at least part of a sample earlier obtained from the subject is lower than or equal to a predetermined reference value.

The method of treatment may also be limited to the decision-making and treatment. Thus, as a configuration of the second aspect, there is provided a method of treatment of a subject having a bladder cancer, comprising:
 α) comparing a sample value corresponding to a level of RBM3 protein in a sample from the subject with a reference value; and,
  if said sample value is equal to or lower than said reference value,
 β) treating said subject with an adjuvant bladder cancer treatment regimen.

Numerous ways of obtaining a sample value corresponding to a level of RBM3 in a sample from a subject are described in the present disclosure.

A subject may have a bladder cancer in such an advanced stage that an adjuvant therapy would normally be considered superfluous and unnecessary painful. However, in such case, a physician may anyway decide to apply the adjuvant therapy if the subject in question has an increased probability of prolonged survival due to a high RBM3 protein value.

Thus, as a configuration of the second aspect, there is provided a method of treatment of a subject having a bladder cancer of an advanced stage, such as TNM stage T3 or T4, comprising:
 a) evaluating an amount of RBM3 in at least part of a sample earlier obtained from the subject and determining a sample value corresponding to the evaluated amount;
 b) comparing said sample value with a predetermined reference value; and
  if said sample value is higher than said reference value,
 c) treating said subject with an adjuvant bladder cancer treatment regimen for prolonged survival.

Further, if said sample value is lower than or equal to said reference value, the subject may be treated with palliative treatment only.

In the context of the present disclosure, the "level of RBM3" refers to the level of RBM3 protein or the level of RBM3 mRNA. The levels of mRNA and protein expression of a certain gene are not always correlated. However, the inventors have noted that the levels of mRNA and protein expression are correlated for the RBM3 gene in various tissues. In the Example below, the RBM3 protein expression is measured. Thus, in preferred embodiments, "RBM3" refers to RBM3 protein.

The skilled person should recognize that the usefulness of the methods according to the above aspects is not limited to the quantification of any particular variant of the RBM3 protein or RBM3 mRNA present in the subject in question, as long as the protein is encoded by the relevant gene and presents the relevant pattern of expression.

As a non-limiting example, the RBM3 protein may comprise a sequence selected from:
 i) SEQ ID NO:1; and
 ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:1.

As another non-limiting example, the RBM3 protein may comprise, or consists of, a sequence selected from:
 i) SEQ ID NO:2; and
 ii) a sequence which is at least 85% identical to SEQ ID NO:2.

In some embodiments, sequence ii) above is at least 90% identical, at least 91% identical, at least 92% identical, at least 93% identical, at least 94° A) identical, at least 95% identical, at least 96% identical, at least 97 identical, at least 98% identical or at least 99% identical to SEQ ID NO:2.

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acid residues may at the most be 85% identical to a target sequence of 100 amino acid residues.

Regarding step a) of the methods of the present disclosure, an increase in the amount of RBM3 typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of RBM3 protein will not result in a decrease in the sample value in the context of the present disclosure.

However inconvenient, but in an equivalent fashion, the evaluated amounts may be inversely related to sample values if the qualification between step b) and c) is inverted. For example, the qualification between step b) and c) is inverted if the phrase "if the sample value is higher than the reference value" is replaced with "if the sample value is lower than the reference value".

In the context of the present disclosure, "prognosis" refers to the prediction of the course or outcome of a disease and its treatment. For example, prognosis may also refer to a determination of chance of survival or recovery from a disease, as well as to a prediction of the expected survival time of a subject. A prognosis may specifically involve establishing the likelihood for survival of a subject during a period of time into the future, such as three years, five years, ten years or any other period of time. A prognosis may further be represented by a single value or a range of values.

Further, in the context of the methods of the present disclosure, "earlier obtained" refers to obtained before the method is performed. Consequently, if a sample earlier obtained from a subject is used in a method, the method does not involve obtaining the sample from the subject, i.e., the sample was previously obtained from the subject in a step separate from the method.

The methods and uses of the present disclosure, except the methods of treatment, may unless otherwise stated be carried out entirely ex vivo.

Further, in the context of the present disclosure, "a mammalian subject having a bladder cancer" refers to a mammalian subject having a primary bladder tumor or a mammalian subject which has had a primary bladder tumor removed, wherein the removal of the tumor refers to eradicating the tumor by any appropriate type of surgery or therapy. In the method and use aspects of the present disclosure, "a mammalian subject having a bladder cancer" also includes the cases wherein the mammalian subject is suspected of having a bladder cancer at the time of the use or the performance of the method and the bladder cancer diagnosis is established later.

Further, in the context of the present disclosure, the "predetermined reference value" refers to a predetermined value found to be relevant for making decisions or drawing conclusions regarding the prognosis or a suitable treatment strategy for the subject.

Also, in the context of the present disclosure, a reference value being "associated" with a reference prognosis refers to the reference value being assigned a corresponding reference prognosis, based on empirical data and/or clinically relevant assumptions. For example, the reference value may be the average RBM3 value in a relevant group of subjects and the reference prognosis may be an average survival in the same group. Further, the reference value does not have to be assigned to a reference prognosis directly derived from prognosis data of a group of subjects exhibiting the reference value. The reference prognosis may for example correspond to the prognosis for subjects exhibiting the reference value or lower. That is, if the reference value is 1 on a scale from 0 to 2, the reference prognosis may be the prognosis of the subjects exhibiting the values 0 or 1. Consequently, the reference prognosis may also be adapted to the nature of the available data. As further discussed above, the reference prognosis may be further adapted to other parameters as well.

Step a) of the methods of the above aspects involve evaluating an amount of RBM3 present in at least part of the sample, and determining a sample value corresponding to the amount. The "at least part of the sample" refers to a relevant part or relevant parts of the sample for establishing the prognosis or drawing conclusions regarding suitable treatments. The person skilled in the art understands which part or parts that are relevant under the circumstances present when performing the method. For example, if evaluating a sample comprising cells, the skilled person may only consider the tumor cells, or only the nuclei of tumor cells, of the sample.

Further, in step a) an amount is evaluated and a sample value corresponding to the amount is determined. Consequently, an exact measurement of the amount of RBM3 is not required for obtaining the sample value. For example, the amount of RBM3 may be evaluated by visual inspection of a prepared and stained tissue sample and the sample value may then be categorized as for example high or low based on the evaluated amount.

The person of skill in the art understands that the evaluation and determination of step a) involves some kind of processing or manipulation of the sample obtained from the subject. It is not possible to determine the sample value by mere inspection. Various techniques, of which some are presented below, for such evaluation and determination are well known to the skilled person. The methods of the present disclosure are therefore not limited to any specific technique or techniques for the performance of step a).

The treatment regimen of the present disclosure may comprise or consist of surgery, such as radical cystectomy.

Further, the treatment regimen of the present disclosure may be an adjuvant and/or a neo-adjuvant therapy. Such a treatment regimen may for example comprise or consist of chemotherapy and/or administration of Bacillus Calmette-Guérin (BCG). Examples of chemotherapies are applications of epirubicin, gemcitabine and/or mitomycin. Other examples of chemotherapies are platinum-based treatments, such as application of carboplatin, paraplatin, oxaliplatin, satraplatin, picoplatin or cisplatin. Still other examples of chemotherapeutic agents that may be applied are docetaxel, methotrexate, vinblastine, doxorubicin, mitomycin C, thiotepa, valrubicin, and vinflunine.

Cisplatin may for example be applied in combination with methotrexate, vinblastine and/or doxorubicin. A combination of all of these agents (sometimes referred to as MVAC) may be applied in cases of advanced disease (of poor prognosis), even though normally associated with severe side-effects. Cisplatin may also be applied in combination with gemcitabine. Gemcitabine may also be applied in combination with carboplatin, in particular when the subject is intolerant of cisplatin.

Further, the treatment regimen may comprise biological therapy, such as application of interleukin 2, sorafenib, sunitinib or lapatinib. The biological treatment may be combined with chemotherapy The treatment regimen may also comprise or consist of radiation therapy. Chemotherapy and/or biological therapy may be carried out before or after radiation therapy.

Figure 1B:
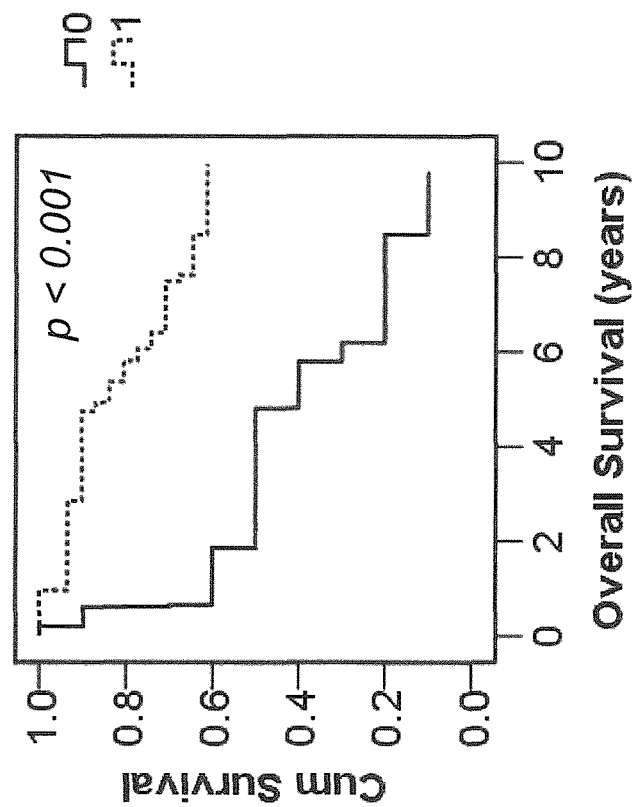
FIG. 1B shows overall survival (OS) of patients with early stage urothelial cancer (stage Ta or T1), i.e. 44 subjects. Patients were divided into two groups based on RBM3 expression. The solid line represents patients with low RBM3 expression (NS≤3) and the dotted line represents patients with high RBM3 expression (NS>3).

If a subject is diagnosed with early stage bladder cancer, it may be difficult for the physician responsible for the treatment to decide whether to apply cystectomy or not. As seen in FIG. 1b, a group of early stage bladder cancer subjects having a relatively poor prognosis may be identified with a method according to the present disclosure. Subjects having such a poor prognosis may be considered eligible for cystectomy even though their cancer is of an early stage. In other words, the inventive methods may be particularly relevant for a subject having an early stage bladder cancer, such as a cancer of TNM stage Ta or T1.

Further, it may be difficult for a physician to decide whether to apply neoadjuvant chemotherapy or not to a subject having a stage T2 bladder cancer. In such a case, a low RBM3 value may advise the physician to apply the neoadjuvant chemotherapy while a high RBM3 value may advise may the physician to refrain from such a treatment. Thus, an RBM3 low T2N0 bladder cancer subject may be given neoadjuvant therapy even though subjects having cancers of that stage are normally not given such treatment. Thus, in some embodiments of the present disclosure, the bladder cancer is of stage T2.

In embodiments of the present disclosure, the prognosis may be a probability of survival, and there are several ways to measure "survival". The survival of the present disclosure may for example be overall survival (see the figures), recurrence free survival or bladder cancer specific survival (the skilled person is familiar with these terms). Further, the "survival" may be measured over different periods, such as five, ten or 15 years. Accordingly, the survival may be a five-year, ten-year or 15-year survival. The skilled person understands that when a reference prognosis is employed, it is of the same type as the prognosis for the subject.

In embodiments of the methods of the above aspects, the sample may be a body fluid sample. For example, the body fluid sample may be selected from the group consisting of blood, plasma, serum, cerebral fluid, urine, lymph, seminal fluid and exudate. Alternatively, the sample may be a cytology sample or a stool sample.

The level of RBM3 protein expression may preferably be measured intracellularly. Thus, the body fluid, cytology or stool sample may for example comprise cells, such as tumor cells.

In further embodiments of the methods of the above aspects, the sample may be a tissue sample, such as an bladder tissue sample, such as an bladder tumor tissue sample, e.g, from a biopsy or surgically removed specimen. Thus, the sample may be obtained and the inventive method carried out after transurethral resection of the bladder.

RBM3 protein is found both in the nucleus and in the cytoplasm. The inventors have however noted that nuclear expression of RBM3 protein is particularly relevant for determining prognoses or selecting treatments (see the figures). Thus, the evaluation of step a) may be limited to the nuclei of cells, such as tumor cells, of said sample. Consequently, when a tissue sample is examined, only the nuclei of tumor cells may be taken into consideration. Such examination may for example be aided by immunohistochemical staining.

The tissue samples in the Example below are from male and female humans, and the inventors have found that the RBM3 protein expression is prognostically relevant independent of the subject's sex. Accordingly, the subject of the methods of the above aspects may be a human, and further, the subject of the methods of the above aspects may be male or female.

A sample value of RBM3 being higher than the reference value, or a subject from which such sample value is obtained, is sometimes herein referred to as being "RBM3 high". Further, a sample value of RBM3 being lower than, or equal to, the reference value, or a subject from which such sample value is obtained, is sometimes herein referred to as being "RBM3 protein low".

In the context of the present disclosure, the terms "sample value" and "reference value" are to be interpreted broadly. The quantification of RBM3 to obtain these values may be done via automatic means, via a scoring system based on visual or microscopic inspection of samples, or via combinations thereof. However, it is also possible for a skilled person, such as a person skilled in the art of histopathology, to determine the sample and reference values by inspection, e.g., of tissue slides that have been prepared and stained for RBM3 protein expression.

Determining that the sample value is higher than the reference value may thus be determining, upon visual or microscopic inspection, that a sample tissue slide is more densely stained and/or exhibit a larger fraction of stained cells than a reference tissue slide. The sample value may also be compared to a reference value given by a literal reference, such as a reference value described in wording or by a reference picture. Consequently, the sample and/or reference values may in some cases be mental values that the skilled person envisages upon inspection and comparison.

One or more of the steps of the methods of the present disclosure may be implemented in an apparatus. For example, step a) and optionally step b) may be performed in an automatic analysis apparatus, and such an apparatus may be based on a platform adapted for immunohistochemical analysis. As an example, one or more tumor tissue sample(s) from the subject in question may be prepared for immunohistochemical analysis manually and then loaded into the automatic analysis apparatus, which gives the sample value of step a) and optionally also performs the comparison with the reference value of step b). The operator performing the analysis, the physician ordering the analysis or the apparatus itself may then draw the conclusion of step c). Consequently, software adapted for drawing the conclusion of step c) may be implemented on the apparatus.

A reference value, which is relevant for establishing a prognosis or making a treatment decision regarding bladder cancer subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant prognostic information, e.g., the largest separation between the RBM3 high survival curve and the RBM3 low survival curve (see the figures), which corresponds to the largest difference in survival between the first and the second group of the first aspect. Alternatively, the reference value may be selected such that a group of subjects having particularly good prognoses or particularly poor prognoses is singled out.

In embodiments of the methods of the above aspects, the reference value may correspond to the amount of RBM3 in a healthy tissue from the subject of the method. As another example, the reference value may be provided by the amount of RBM3 measured in a standard sample of normal tissue from another, comparable subject. As another example, the reference value may be provided by the amount of RBM3 measured in a reference sample comprising tumor cells, such as a reference sample of bladder tumor tissue. The amount of protein expression of the reference sample may preferably be previously established. Consequently, the reference value may be provided by the amount of RBM3 measured in a reference sample comprising cells expressing a predetermined amount of RBM3.

Further, the reference value may for example be provided by the amount of RBM3 protein expression measured in a reference sample comprising cell lines, such as cancer cell lines, expressing a predetermined, or controlled, amount of RBM3 protein. The person skilled in the art understands how to provide such cell lines, for example guided by the disclosure of Rhodes et al. (2006) *The biomedical scientist*, p 515-520.

Consequently, in embodiments of the methods of the present disclosure, the reference value may be a predetermined value corresponding to the amount of RBM3 in a reference sample.

However, as discussed further below, the amount of RBM3 protein in the reference sample does not have to directly correspond to the reference value. The reference sample may also provide an amount of RBM3 protein that helps a person performing the method to assess various reference values. For example, the reference sample(s) may help in creating a mental image of the reference value by providing a "positive" reference value and/or a "negative" reference value.

One alternative for the quantification of RBM3 protein expression in a sample, such as the sample earlier obtained from the subject or the reference sample, is the determination of the fraction of cells in the sample that exhibit RBM3 protein expression over a certain level. The fraction may for example be: a "cellular fraction", wherein the RBM3 protein expression of the whole cells is taken into account; a "cytoplasmic fraction", wherein the RBM3 protein expression of only the cytoplasms of the cells is taken into account; or a "nuclear fraction", wherein the RBM3 protein expression of only the nuclei of the cells is taken into account. The nuclear fraction may for example be classified as <2%, 2-25%, >25-75% or >75% immunoreactive cells of the relevant cell population. The "nuclear fraction" corresponds to the percentage of relevant cells in a sample that exhibits a positive staining in the nucleus, wherein a medium or distinct and strong immunoreactivity in the nucleus is considered positive and no or faint immunoreactivity in the nucleus is considered negative. The person skilled in the art of pathology understands which cells that are relevant under the conditions present when performing the method and may determine a nuclear fraction based on his general knowledge and the teachings of the present disclosure. The relevant cells may for example be tumor cells. Further, the skilled artisan understands how to perform corresponding measurements employing the "cytoplasmic fraction" or "cellular fraction".

Another alternative for the quantification of RBM3 protein expression in a sample, such as the sample earlier obtained from the subject or the reference sample, is the determination of the overall staining intensity of the sample. The intensity may for example be: a "cellular intensity", wherein the RBM3 protein expression of the whole cells is taken into account; a "cytoplasmic intensity", wherein the RBM3 protein expression of only the cytoplasms of the cells is taken into account, or a "nuclear intensity", wherein the RBM3 protein expression of only the nuclei of the cells is taken into account. Nuclear intensity is subjectively evaluated in accordance with standards used in clinical histopathological diagnostics. Outcome of a nuclear intensity determination may be classified as: absent=no overall immunoreactivity in the nuclei of relevant cells of the sample, weak=faint overall immunoreactivity in the nuclei of relevant cells of the sample, moderate=medium overall immunoreactivity in the nuclei of relevant cells of the sample, or strong=distinct and strong overall immunoreactivity in the nuclei of relevant cells of the sample. The person skilled in the art understands which cells that are relevant under the conditions present when performing the method and may determine a nuclear intensity based on his general knowledge and the teachings of the present disclosure. The relevant cells may for example be tumor cells. Further, the skilled artisan understands how to perform corresponding measurements employing the "cytoplasmic intensity" or "cellular intensity".

The inventors have found that nuclear expression of RBM3 protein is particularly relevant for establishing prognoses.

Thus, in embodiments of the methods of the above aspects, the reference value may be a nuclear fraction, a nuclear intensity or a combination thereof. Accordingly, the sample value may be a nuclear fraction, a nuclear intensity or a combination thereof.

Thus, in embodiments of the methods of the above aspects, the reference value of step b) is a nuclear fraction of 95% or lower, such as 90 or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Further, in embodiments of the methods of the above aspects the reference value of step b) may be a moderate nuclear intensity of RBM3 protein expression or lower, such as a weak nuclear intensity of RBM3 protein expression or lower, such as an absent nuclear of RBM3 protein expression.

Also, in embodiments of the methods of the above aspects, the reference value may be a combination or a function of a fraction value and an intensity value. The reference value may thus involve two, and even more, criteria.

In general, the selection of an intensity value and/or a fraction value as the reference value may depend on the staining procedure, e.g., on the type and amount/concentration of the employed antibody and on the type and concentration of the staining reagents.

Guided by the present disclosure, a person skilled in the art, e.g., a pathologist understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of RBM3 protein for establishing the appearance of a certain fraction or intensity.

However, a reference sample may not only be used for the provision of the actual reference value, but also for the provision of an example of a sample with an amount of RBM3 that is higher than the amount corresponding to the reference value. As an example, in histochemical staining, such as in immunohistochemical staining, the skilled artisan may use a reference sample for establishing the appearance of a stained sample having a high amount of RBM3 protein, e.g., a positive reference. Subsequently, the skilled artisan may assess the appearances of samples having lower amounts of RBM3 protein, such as the appearance of a sample with an amount of RBM3 protein corresponding to the reference value. In other words, the skilled artisan may use a reference sample to create a mental image of a reference value corresponding to an amount of RBM3 protein which is lower than that of the reference sample. Alternatively, or as a complement, in such assessments, the skilled artisan may use another reference sample having a low amount of RBM3 protein, or lacking detectable RBM3 protein, for establishing the appearance of such sample, e.g., as a "negative reference".

For example, if a moderate nuclear intensity is used as the reference value, two reference samples may be employed: a first reference sample having no detectable RBM3 protein, and thus corresponding to an absent nuclear intensity, which is lower than the reference value; and a second reference sample having an amount of RBM3 protein corresponding to a strong nuclear intensity, which is higher than the reference value.

Consequently, in the evaluation, the skilled artisan may use a reference sample for establishing the appearance of a sample with a high amount of RBM3 protein. Such reference sample may be a sample comprising tissue expressing a high amount of RBM3 protein, such as a sample comprising bladder cancer tissue having a pre-established high expression of RBM3 protein.

Accordingly, the reference sample may provide an example of a strong nuclear intensity (NI). With the knowledge of the appearance of a sample with strong NI, the skilled artisan may then divide samples into the NI categories absent, weak, moderate and strong. This division may be further assisted by a reference sample lacking detectable RBM3 protein (negative reference), i.e., a reference sample providing an absent nuclear intensity. Also, the reference sample may provide an example of a sample with a nuclear fraction (NF) higher than 75%. With the knowledge of the appearance of a sample with more than 75% positive cells, the skilled artisan may then evaluate the NF of other samples having e.g., a lower percentage of positive cells. This division may be further assisted by a reference sample essentially lacking RBM3 protein (negative reference), i.e., a reference sample providing a low NF (e.g., <5%, such as <2%), or a NF of 0.

As mentioned above, cell lines expressing a controlled amount of RBM3 protein may be used as the reference, in particular as a positive reference.

One or more pictures may also be provided as the "reference sample". For example, such a picture may show an example of a tumor tissue slide stained with a certain antibody during certain conditions and exhibiting a certain nuclear intensity and/or fraction. The above discussion about the "reference sample" applies mutatis mutandis to pictures.

In some embodiments, step a) of the methods of the above aspects may comprise:

obtaining biological material from the subject, excising or selecting a relevant part of the biological material to obtain said sample and optionally arranging the sample on a solid phase to facilitate the evaluation of step a). Step a) may thus, as an example, comprise obtaining bladder tumor tissue material from the subject, optionally fixating the tissue material in paraffin or formalin, histo-processing the tissue material to obtain a section which constitute said sample and optionally mounting said sample on a transparent slide, such as a glass slide, for microscopy.

In embodiments of the methods of the aspects above, the RBM3 protein may be detected and/or quantified through the application to the sample of a detectable and/or quantifiable affinity ligand, which is capable of selective interaction with the RBM3 protein. The application of the affinity ligand is performed under conditions that enable binding of the affinity ligand to RBM3 protein in the sample.

To concretize, in embodiments of the methods of the aspects above, step a) may comprise:

a1) applying to said sample a quantifiable affinity ligand capable of selective interaction with the RBM3 protein to be evaluated, said application being performed under conditions that enable binding of said affinity ligand to RBM3 protein present in said sample;

a2) removing non-bound affinity ligand; and a3) quantifying the affinity ligand remaining in association with said sample to evaluate said amount.

"Affinity ligand remaining in association with the sample" refers to affinity ligand which was not removed in step a2), e.g., the affinity ligand bound to the sample. Here, the binding may for example be the interaction between antibody and antigen.

However, in some embodiments, the removal of non-bound affinity ligand according to a2), e.g. the washing, is not always necessary. Thus, in some embodiments of the methods of the aspects above, step a) may comprise:

aI) applying to said sample a quantifiable affinity ligand capable of selective interaction with the RBM3 protein to be evaluated, said application being performed under conditions that enable binding of said affinity ligand to RBM3 protein present in said sample;

aII) quantifying the affinity bound to said sample to evaluate said amount.

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity/selectivity does not necessarily require high affinity. Molecules with low affinity (in the molar range) for its counterpart have been shown to be as selective/specific as molecules with much higher affinity. In the case of the present disclosure, a specific or selective interaction refers to the extent to which a particular method can be used to determine the presence and/or amount of a specific protein, the target protein, under given conditions in the presence of other proteins in a tissue sample or fluid sample of a naturally occurring or processed biological fluid. In other words, specificity or selectivity is the capacity to distinguish between related proteins. For example, the specificity or selectivity of an antibody may be determined as in Examples, Section 2, below, wherein analysis is performed using a protein array set-up, a suspension bead array and a multiplexed competition assay, respectively. Specificity and selectivity determinations are also described in Nilsson P et al. (2005) Proteomics 5:4327-4337.

It is regarded as within the capabilities of those of ordinary skill in the art to select or manufacture the proper affinity ligand and to select the proper format and conditions for detection and/or quantification. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof, i.e., affinity ligands based on an immunoglobulin scaffold. The antibodies and the fragments or derivatives thereof may be isolated. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. The polyclonal antibodies may be antigen purified. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g. RBM3 protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Plückthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Plückthun A (1988) Science 240:1038-1041).

In some embodiments, the affinity ligand of the present disclosure is capable of selective interaction with a peptide consisting of the amino acid sequence SEQ ID NO:1. The RBM3 fragment SEQ ID NO:1 was designed to lack transmembrane regions to ensure efficient expression in E. coli, and to lack any signal peptide, since those are cleaved off in the mature protein. SEQ ID NO:1 was thus designed for immunizations. In addition, the protein fragment was designed to consist of a unique sequence with low sequence identity to other human proteins, to minimize cross reactivity of generated affinity reagents, and to be of a suitable size to allow the formation of conformational epitopes and still allow efficient cloning and expression in bacterial systems. Accordingly, in the cases wherein the affinity ligand is an antibody or fragment o derivative thereof, the affinity ligand may be obtainable by a process comprising a step of immunizing an animal with a peptide whose amino acid sequence consists of the sequence SEQ ID NO:1. For example, the immunization process may comprise primary immunization with the protein in Freund's complete adjuvant. Also, the immunization process may further comprise boosting at least two times, in intervals of 2-6 weeks, with the protein in Freund's incomplete adjuvant. Processes for the production of antibodies or fragments or derivatives thereof against a given target are known in the art.

In the context of the present disclosure, an "antigen purified antibody" is one or a population of polyclonal antibodies which has been affinity purified on its own antigen, thereby separating such antigen purified antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain antigen purified antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of RBM3 protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific/selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P Å and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against RBM3 protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269:22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life. Sci. 59:1993-1998); staphylococcal nuclease (Norman T C et al. (1999) Science 285:591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plückthun A (1997) Proc. Natl. Acad. Sci. U.S.A. 94:4937-4942), yeast two-hybrid system (Fields S and Song 0 (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25): 913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

As mentioned above, the RBM3 protein fragment SEQ ID NO:1 was designed to consist of a unique sequence with low sequence identity to other human proteins and to minimize cross reactivity of generated affinity reagents. Consequently, in embodiments of the present disclosure, the affinity ligand may be capable of selective interaction with a polypeptide consisting of the amino acid sequence SEQ ID NO:1.

The epitope regions SEQ ID NO:4 and 5 has been identified within SEQ ID NO:1. Thus, in some embodiments, the affinity ligand of the present disclosure is capable of selective interaction with a peptide consisting of an amino acid sequence selected from SEQ ID NO:4 and 5.

Further, another four epitope regions (SEQ ID NO:6-9) have been identified. Thus, in some embodiments, the affinity ligand of the present disclosure is capable of selective interaction with an RBM3 fragment which consists of 20 amino acid residues or less, such as 15 amino acid residues or less, and comprises a sequence selected from SEQ ID NO:6-9.

Also, another ten epitope regions (SEQ ID NO:10-19) have been identified. Thus, in some embodiments, the affinity ligand of the present disclosure is capable of selective interaction with an RBM3 fragment which consists of 20 amino acid residues or less, such as 15 amino acid residues or less, and comprises a sequence selected from SEQ ID NO:10-19.

Antibodies having selectivity for a single epitope region (such as monoclonal antibodies) may provide for increased reproducibility in detection analyses as compared to antibodies generated against a longer peptide sequence (such as a PrEST or a full-length protein). The antibodies selective for a single epitope region may also provide for distinct and strong staining in immunohistochemical analyses. These benefits, independently or jointly, may be valuable when and making treatment predictions or decisions regarding treatments according to the present disclosure.

The monoclonal antibodies named "6F11" and "1B5" are considered to be particularly beneficial. 6F11 and 1B5 have both been shown to be more selective than a polyclonal anti-RBM3 antibody. Further, 1B5 has been shown to be more selective than 6F11. 1B5 is also employed in the example section below.

SEQ ID NO:17, to which 1B5 binds, is within SEQ ID NO:5. In preferred embodiments of the present disclosure, the affinity ligand is thus capable of selective interaction with an RBM3 fragment which consists of SEQ ID NO:5, and in particularly preferred embodiments of the present disclosure, the affinity ligand is capable of selective interaction with an RBM3 fragment which consists of 20 amino acid residues or less, such as 15 amino acid residues or less, and comprises the sequence SEQ ID NO:17.

6F11 has been shown to bind to SEQ ID NO:8 and SEQ ID NO:16. In other preferred embodiments of the present disclosure, the affinity ligand is thus capable of selective interaction with an RBM3 fragment which consists of 20 amino acid residues or less, such as 15 amino acid residues or less, and comprises a sequence selected from SEQ ID NO:8 and 16. Note that SEQ ID NO:8 and 16 are overlapping and that such a fragment may comprise the sequences of both SEQ ID NO:8 and 16.

In Examples below, antibodies capable of selective interaction with SEQ ID NO:24 and 25 are shown to be particularly selective. In preferred embodiments of the present disclosure, the affinity ligand is thus capable of selective interaction with an RBM3 fragment which consists of a sequence selected from SEQ ID NO:24 and 25.

Further, the epitope regions SEQ ID NO:22 and 26 have been identified. In other preferred embodiments of the present disclosure, the affinity ligand is thus capable of selective interaction with an RBM3 fragment which consists such as 15 amino acid residues or less, such as 10 amino acid residues or less and comprises a sequence selected from SEQ ID NO:22 and 26.

The detection and/or quantification of the affinity ligand capable of selective interaction with the RBM3 protein may be accomplished in any way known to the skilled person for detection and/or quantification of binding reagents in assays based on biological interactions. Accordingly, any affinity ligand described above may be used to quantitatively and/or qualitatively detect the presence of the RBM3 protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with RBM3 protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g., $^3H$, $^{14}C$, $^{32}P$, $^{35}S$ or $^{125}I$) and particles (e.g., gold). In the context of the present disclosure, "particles" refer to particles, such as metal particles, suitable for labeling of molecules. Such particles are well known to the skilled person. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech*. 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its RBM3 protein target may involve visualizing techniques, such as light microscopy or immunofluoresence microscopy. Other methods may involve the detection via flow cytometry or luminometry.

Biological material from the subject may be used for obtaining the sample for detection and/or quantification of RBM3 protein. The sample may thus be an earlier obtained sample. If using an earlier obtained sample in a method, no steps of the method are practiced on the human or animal body.

The affinity ligand may be applied to the sample for detection and/or quantification of the RBM3 protein. This procedure enables not only detection of RBM3 protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from a chemical reaction. Those of skill in the art are aware that a variety of different protocols can be modified in order for proper detection and/or quantification.

In embodiments of the methods of the above aspects, the sample may be immobilized onto a solid phase support or carrier, such as nitrocellulose or any other solid support matrix capable of immobilizing RBM3 protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, primary affinity ligand selective for RBM3 protein may be applied. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of a1) or aI) may be detected using a secondary affinity ligand capable of recognizing the quantifiable affinity ligand. The quantification of a3) or aII) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the RBM3 protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the RBM3 protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^3H$, $^{14}C$, $^{32}P$, $^{35}S$ or $^{125}I$. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize RBM3 protein by detection of radioactivity in vivo or ex vivo. Radionuclear scanning with e.g., gamma camera, magnetic resonance spectroscopy or emission tomography function for detection in vivo and ex vivo, while gamma/beta counters, scintillation counters and radiographies are also used ex vivo.

Methods for detecting and quantifying biomarkers on the mRNA level are well known within the art.

According to one such method, total cellular RNA is purified from cells by homogenization in the presence of nucleic acid extraction buffer, followed by centrifugation. Nucleic acids are then precipitated, in order to remove DNA by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual (Sambrook J. et al., (1989) 2nd edition, Cold Spring Harbor Laboratory Press). Methods for the preparation of labeled DNA and RNA probes, and the conditions for hybridization thereof to target nucleotide sequences, are described in Molecular Cloning: A Laboratory Manual (Sambrook J. et al., (1989) 2nd edition, Cold Spring Harbor Laboratory Press). For example, the nucleic acid probe may be labeled with, e.g., a radionuclide such as $^3H$, $^{32}P$, $^{33}P$, $^{14}C$, or $^{35}S$; a heavy metal; or a ligand capable of functioning as a specific binding pair member for a labeled ligand (e.g., biotin, avidin, or an antibody), a fluorescent molecule, a chemiluminescent molecule, an enzyme, or the like.

Probes may be labeled to high specific activity by either the nick translation method (Rigby et al., (1977) J. Mol Biol, 113: 237-251), or by the random priming method (Fienberg, (1983) Anal. Biochem., 132: 6-13). The latter can be a method for synthesizing $^{32}P$-labeled probes of high specific activity from RNA templates. For example, by replacing preexisting nucleotides with highly radioactive nucleotides according to the nick translation method, it is possible to prepare $^{32}P$-labeled nucleic acid probes with a specific activity well in excess of 10 cpm/microgram. Autoradiographic detection of hybridization then can be performed by exposing hybridized filters to photographic film. Densitometric scanning of the photographic films exposed by the hybridized filters provides an accurate measurement of biomarker levels. Using another approach, biomarker levels can be quantified by computerized imaging systems, such as the Molecular Dynamics 400-B 2D Phosphorimager (Amersham Biosciences, Piscataway, N.J., USA).

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcript may be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects.

The relative number of RNA transcripts in cells also can be determined by reverse transcription of RNA transcripts, followed by amplification of the reverse-transcribed transcripts by polymerase chain reaction (RT-PCR). The levels of RNA transcripts can be quantified in comparison with an internal standard, for example, the level of mRNA from a standard gene present in the same sample. The person skilled in the art is capable of selecting suitable genes for use as an internal standard. The methods for quantitative RT-PCR and variations thereof are within the skill in the art.

Any suitable primers can be used for the quantitative RT-PCR. Preferably, the primers are specific to RBM3. It is within the skill in the art to generate primers specific to RBM3 (e.g. starting from SEQ ID NO:3). Primers can be of any suitable length, but are preferably between 19 and 23 (e.g., 19, 20, 21, 22, or 23) nucleotides. Ideally, amplicon length should be 50 to 150 (up to 250 may be necessary but then optimization of the thermal cycling protocol and reaction components may be necessary) bases for optimal PCR efficiency. Designing primers that generate a very long amplicon may lead to poor amplification efficiency. Information about primer design and optimal amplicon size may fo example be found at www.ambion.com.

In some instances, it may be desirable to use microchip technology to detect biomarker expression. The microchip can be fabricated by techniques known in the art. For example, probe oligonucleotides of an appropriate length, e.g., 40 nucleotides, are 5'-amine modified at position C6 and printed using commercially available microarray systems, e.g., the GENEMACHINE OmniGrid 100 Microarrayer and Amersham CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6 times SSPE/30% formamide at 25° C. for 18 hours, followed by washing in 0.75 times TNT at 37° C. for 40 minutes. At positions on the array, where the immobilized probe DNA recognizes a complementary target cDNA in the sample, hybridization occurs. The labeled target cDNA marks the exact position on the array where binding occurs, thereby allowing automatic detection and quantification. The output consists of a list of hybridization events, which indicate the relative abundance of specific cDNA sequences, and therefore the relative abundance of the corresponding complementary biomarker, in the subject sample. According to one embodiment, the labeled cDNA oligomer is a biotin-labeled cDNA prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding biomarker in the subject sample.

The use of the array has one or more advantages for mRNA expression detection. First, the global expression of several to thousands of genes can be identified in a single sample at one time. Second, through careful design of the oligonucleotide probes, the expression of both mature and precursor molecules can be identified. Third, in comparison with Northern blot analysis, the chip requires a small amount of RNA.

The RBM3 mRNA may for example be extracted from formalin-fixed, paraffin-embedded tumor tissue. Accordingly, the sample of the methods of the present disclosure may be formalin-fixed and/or paraffin-embedded bladder tumor tissue independent of if RBM3 protein or RBM3 mRNA is detected.

The inventors have realized that RBM3 mRNA analysis of the present disclosure may be incorporated in an mRNA-based assay designed to support individualized treatment planning. Such an assay may employ RT-PCR to analyze the expression of several genes.

Following the findings presented above, the inventors have realized several uses for the RBM3 protein and fragments thereof.

As a third aspect of the present disclosure, there is provided a use of an RBM3 protein as a prognostic marker for bladder cancer. The protein is preferably provided in a sample, such as a bladder cancer tissue sample, from a subject having a bladder cancer.

Normally, the RBM3 protein of the third aspect will be used as a marker of a relatively good bladder cancer prognosis.

The use of the third aspect may be entirely ex vivo.

In the context of the present disclosure, "prognostic marker" refers to something material which presence indicates a prognosis. The marker may thus be a biomarker, such as a human protein.

As a fourth aspect or the present disclosure, there is provided a use of an RBM3 protein, or an antigenically active fragment thereof, for the production, selection or purification of a prognostic agent for a mammalian subject having a bladder cancer.

In the context of the present disclosure, an "antigenically active fragment" of an RBM3 protein is a fragment of sufficient size to be useful for the generation of an affinity ligand, e.g., an antibody, which selectively interacts with an RBM3 protein comprising the fragment.

The selection and purification may be ex vivo, while the production may be in vivo (in an animal).

In the context of the present disclosure, "prognostic agent" refers to an agent having at least one property being valuable in an establishment of a prognosis, e.g., a prognosis for a mammalian subject having a bladder cancer. For example, the prognostic agent may be capable of selective interaction with the prognostic marker.

The prognostic agent may be an affinity ligand capable of selective interaction with the RBM3 protein or the antigenically active fragment thereof. Examples of such affinity ligands are discussed above in connection with the method aspects.

Guided by the teachings of the present disclosure, the person skilled in the art understands how to use the RBM3 protein or fragment in the production, selection or purification of the prognostic agent. For example, the use may comprise affinity purification on a solid support onto which the RBM3 protein has been immobilized. The solid support may for example be arranged in a column. Further, the use may comprise selection of affinity ligands having specificity for the RBM3 protein using a solid support onto which the polypeptide has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity for the immobilized RBM3 protein of a number of potential affinity ligands.

Also, for the production of the prognostic agent, the RBM3 protein or an antigenically active fragment thereof may be used in an immunization of an animal, such as a rabbit or mouse.

Such use may be involved in a method comprising the steps:
i) immunizing an animal using the RBM3 protein or antigenically an active fragment thereof as the antigen;
ii) obtaining serum comprising the prognostic agent from the immunized animal; and, optionally,
iii) isolating the prognostic agent from the serum.

Alternatively the steps following the first step may be:
ii') obtaining cells from the immunized animal, which cells comprise DNA encoding the prognostic agent,
iii') fusing the cells with myeloma cells to obtain at least one clone, and
iv') obtaining the prognostic agent expressed by the clone.

In embodiments of the third or fourth aspect, the amino acid sequence of the RBM3 protein may comprise a sequence selected from:
i) SEQ ID NO:1; and
ii) a sequence which is at least 85% identical to SEQ ID NO:1.

In some embodiments, sequence ii) is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

Further, in embodiments of the sixth aspect the amino acid sequence of the RBM3 protein may comprise or consist of a sequence selected from:
i) SEQ ID NO:2; and
ii) a sequence which is at least 85% identical to SEQ ID NO:2.

In some embodiments, sequence ii) is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2.

The antigenically active fragment of the fourth aspect may for example be an RBM3 protein fragment which consists of 50 amino acid residues or less and comprises a sequence selected from SEQ ID NO:4-19 and 22-26. In embodiments of the fourth aspect, the fragment consists of 29 amino acid residues or less. In further embodiments of the fourth aspect, the fragment consists of 21 amino acid residues or less, such as 15 amino acid residues or less, and comprises a sequence selected from SEQ ID NO:6-19 and 22-26.

Also, in connection with the fourth aspect, there is provided a RBM3 protein fragment (as such) consisting of 21 amino acid residues or less and comprising a sequence selected from SEQ ID NO:22-26. The RBM3 protein fragment may for example consist of 15 amino acid residues or less and comprise a sequence selected from SEQ ID NO: 22, 24, 25 and 26. As a further example, the RBM3 protein fragment consists of 10 amino acid residues or less and comprises a sequence selected from SEQ ID NO: 22 and 26.

Different embodiments of an affinity ligand capable of selective interaction with a RBM3 protein or a fragment thereof are discussed above in connection with the method aspects.

As a fifth aspect of the present disclosure, there is provided a use of such an affinity ligand as bladder cancer prognostic agent. Consequently, the affinity ligand may be used for establishing a prognosis for a subject having a bladder cancer. Such use may for example be performed ex vivo, e.g., involving the determination of the amount of RBM3 in at least part of a sample earlier obtained from the subject.

In connection with the fifth aspect, there is provided an affinity ligand (as such) capable of selective interaction with a RBM3 protein fragment consisting of 21 amino acid residues or less and comprising a sequence selected from SEQ ID NO: 22-26. Such affinity ligands (in particular monoclonal antibodies) are described in Examples below. As an example, the affinity ligand is capable of selective interaction with a RBM3 protein fragment consisting of 15 amino acid residues or less and comprising a sequence selected from SEQ ID NO: 22, 24, 25 and 26. As a further example, the affinity ligand is capable of selective interaction with a RBM3 protein fragment consisting of 10 amino acid residues or less and comprising a sequence selected from SEQ ID NO: 22 and 26. Also, the affinity ligand may be capable of selective interaction with a RBM3 protein fragment consisting of 6 amino acid residues or less and comprising the sequence SEQ ID NO: 22.

EXAMPLES

1. Bladder Cancer TMA, Cohort I
a) Material and Methods

Tumor material was collected from 59 patients diagnosed with urothelial cancer in the Department of Pathology, UMAS, during 2000. The median age of patients was 73 (48-91) years. There were 49 male and 10 female patients. The tumor samples were evenly distributed between grades, with 18 well differentiated (grade 1), 17 moderately differentiated (grade 2), and 24 poorly differentiated (grade 3) tumors. The majority of samples were of stage Ta (33/59), 11 were stage T1, 13 stage T2, and 3 were stage T3. Median follow-up time was 6.2 years. Permission for this study was obtained from the Ethics Committee at Lund University.

Prior to TMA construction, all available haematoxylin and eosin stained slides from each case were histopathologically re-evaluated. A standard set of 4×1 mm cores were taken from each invasive tumor in a proportional fashion. A semi-automated arraying device was used (TMArrayer; Pathology Devices, Inc, Westminster, Md., USA).

For the immunohistochemical analysis of RBM3, four μm TMA-sections were automatically pretreated using the PT-link system (DAKO, Copenhagen, Denmark) and then stained in a Techmate 500 (DAKO, Copenhagen, Denmark) with the RBM3 mouse monoclonal antibody 1B5, obtained as previously described (see Examples, sections 3, 6 and 11 of WO 2010/092190), diluted 1:10000

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of i) subcellular localization (nuclear and/or cytoplasmic/membranous), ii) staining intensity (SI) and iii) fraction of stained cells (FSC). RBM3 was mainly expressed in the tumor cell nuclei. Staining intensity was subjectively evaluated in accordance to standards used in clinical histo-pathological diagnostics and outcome was classified as: absent=no immunoreactivity (SI=0), weak=faint immunoreactivity (SI=1), moderate=medium immunoreactivity (SI=2), or strong=distinct and strong immunoreactivity (SI=3). Also fraction of stained cells was subjectively evaluated in accordance to standards used in clinical histo-pathological diagnostics and outcome was classified as: <2%, 2-25%, >25-75% or >75% immunoreactive cells of the relevant cell population (FSC ranging from 0-3). The skilled artisan will recognize that this annotation procedure is similar to a calculation of an Allred score, see e.g. Allred et al (1998) Mod Pathol 11(2), 155.

For statistical analyses, a combined nuclear score (NS) was calculated as the nuclear SI×FSC, whereby NS=0-1 was defined as low expression, NS=2-4 was defined as moderate expression, and NS>4 was defined as strong expression. Based on the survival trends for individual strata, dichotomized variables were constructed for further statistical analyses. A high nuclear score was defined as NS>4, and a low staining score was defined as NS≤4. The above classifications of samples were used for overall survival (OS) analysis according to the Kaplan-Meier method, and the log-rank test was used to compare survival in different strata. Cox regression proportional hazards models were used to estimate the impact of RBM3 expression on OS in both univariate and multivariate analysis, after adjusting for stage and grade. All statistical tests were two-sided, and p-values of <0.05% were considered significant. All calculations were made with the statistical package SPSS 19.0 (SPSS Inc. Illinois, USA).

b) Results

Initial analysis of the cohort revealed that 7-year OS for all patients was approximately 40%. There was an inverse correlation between RBM3 expression and both T-stage and grade (Spearmans Rho, p=0.001). Survival analysis of the entire cohort revealed that the fraction of stained tumor cells positive for anti-RBM3 significantly correlated with OS (FIG. 1A), i.e. a high RBM3 protein level corresponded to an improved survival.

Interestingly, the correlation between the RBM3 protein level and OS was significant when the group of patients having stage Ta or T1 tumors was analyzed (FIG. 1B). Consequently, patients diagnosed with early stage urothelial tumors may be particularly suitable for the analysis of the level of RBM3.

Cox regression univariate analysis showed that increased RBM3 expression was associated with improved OS(RR=0.27, 95% CI: 0.14-0.55, P<0.001) in the present cohort (the Table). Multivariate analysis showed that increased RBM3 expression was associated with improved OS independent of stage and grade (RR=0.29, 95% CI: 0.14-0.63, P=0.002) in the same cohort (the Table).

TABLE

| RBM3 | Univariate | | Multivariate* | |
|---|---|---|---|---|
| | RR (95% CI) | P-value | RR (95% CI) | P-value |
| Low | 1.00 | | 1.00 | |
| High | 0.27 (0.14-0.55) | <0.001 | 0.29 (0.14-0.63) | 0.002 |

*Adjusted for stage and grade

2. Bladder Cancer TMA, Cohort II a) Material and Methods

Tumor material was collected from 98 patients diagnosed with urothelial cancer in the Department of Pathology, UMAS, from Oct. 1, 2002 until Dec. 31, 2003. The median age of patients was 73 (39-90) years. There were 71 (72%) male and 27 (28%) female patients. The tumor samples included 14 well differentiated (grade 1), 30 moderately differentiated (grade 2), and 54 poorly differentiated (grade 3) tumors. There were 40 stage Ta tumors, 22 stage T1, 35 stage T2, and 1 stage T3 tumor. Median follow-up time was 5.8 years. Permission for this study was obtained from the Ethics Committee at Lund University.

Prior to TMA construction, all available haematoxylin and eosin stained slides from each case were histopathologically re-evaluated. A standard set of 2×1 mm cores were taken from each invasive tumor in a proportional fashion. A semi-automated arraying device was used (TMArrayer; Pathology Devices, Inc, Westminster, Md., USA).

For the immunohistochemical analysis of RBM3, four µm TMA-sections were automatically pretreated using the PT-link system (DAKO, Copenhagen, Denmark) and then stained in a Techmate 500 (DAKO, Copenhagen, Denmark) with the RBM3 mouse monoclonal antibody 1B5, obtained as previously described (see Examples, sections 3, 6 and 11 of WO 2010/092190), diluted 1:10000

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of i) subcellular localization (nuclear and/or cytoplasmic/membranous), ii) staining intensity (SI) and iii) fraction of stained cells (FSC). RBM3 was mainly expressed in the tumor cell nuclei. Staining intensity was subjectively evaluated in accordance to standards used in clinical histo-pathological diagnostics and outcome was classified as: absent=no immunoreactivity (SI=0), weak=faint immunoreactivity (SI=1), moderate=medium immunoreactivity (SI=2), or strong=distinct and strong immunoreactivity (SI=3). Also fraction of stained cells was subjectively evaluated in accordance to standards used in clinical histo-pathological diagnostics and outcome was classified as: <2%, 2-25%, >25-75% or >75% immunoreactive cells of the relevant cell population (FSC ranging from 0-3). The skilled artisan will recognize that this annotation procedure is similar to a calculation of an Allred score, see e.g. Allred et al (1998) Mod Pathol 11(2), 155.

For statistical analyses, a combined nuclear score (NS) was calculated as the nuclear SI×FSC, whereby NS=0-1 was defined as low expression, NS=2-4 was defined as moderate expression, and NS>4 was defined as strong expression. Based on the survival trends for individual strata, dichotomized variables were constructed for further statistical analyses. A high nuclear score was defined as NS>1 and a low staining score was defined as NS≤1 The above classifications of samples were used for overall survival (OS) analysis according to the Kaplan-Meier method, and the log-rank test was used to compare survival in different strata. Cox regression proportional hazards models were used to estimate the impact of RBM3 expression on OS in univariate analysis. All statistical tests were two-sided, and p-values of <0.05 were considered significant. All calculations were made with the statistical package SPSS 19.0 (SPSS Inc. Illinois, USA).

b) Results

Figure 2:
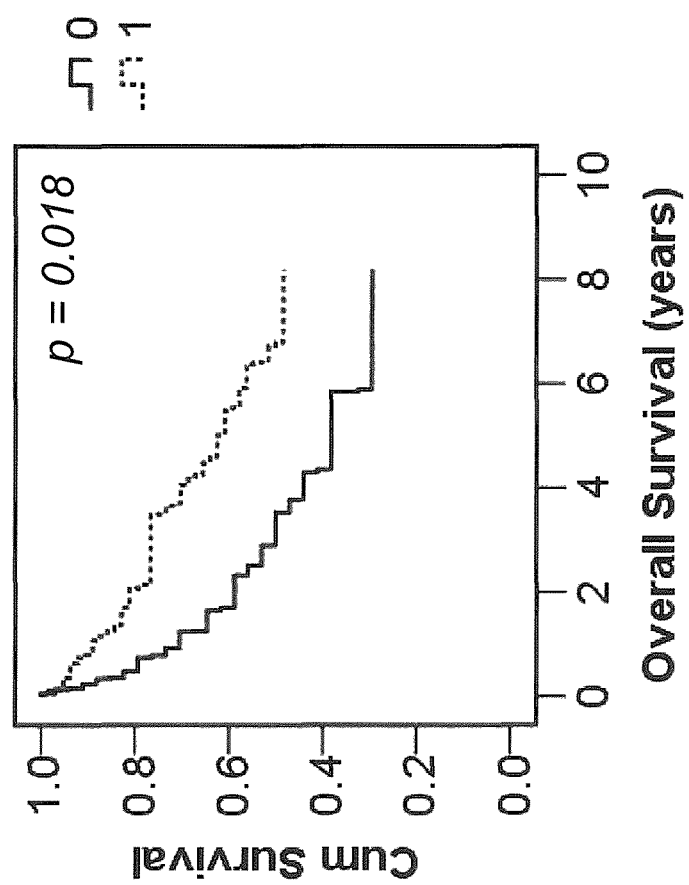
FIG. 2 shows the impact of RBM3 expression on overall survival (OS) of all patients in cohort II, i.e. 98 subjects, diagnosed with urothelial cancer. Patients were divided into two groups based on RBM3 expression. The solid line represents patients with low RBM3 expression, nuclear score (NS)≤1, and the dotted line represents patients with high RBM3 expression (NS>1).
Figure 3B:
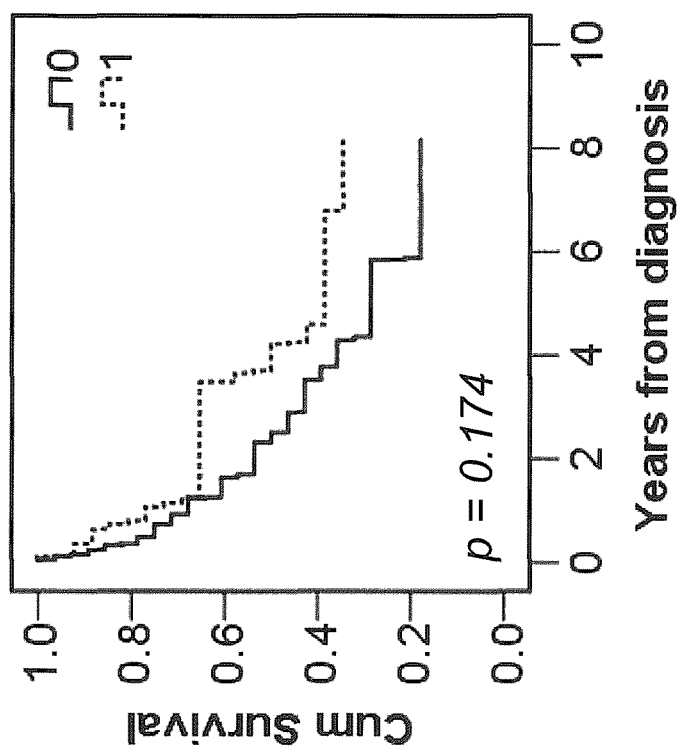
FIG. 3B shows the overall survival in 54 subjects having urothelial cancer of grade 3.
Figure 3A:
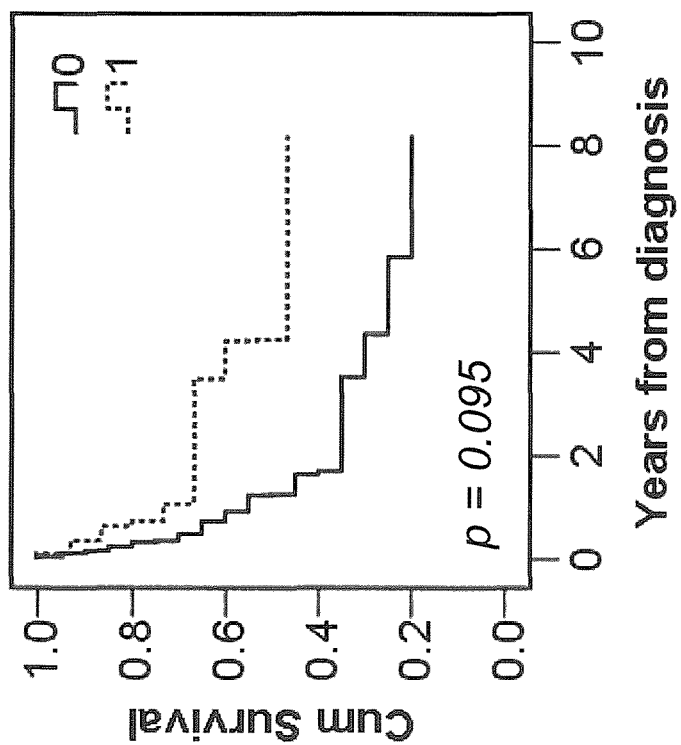
FIG. 3A shows the overall survival in 35 subjects having urothelial cancer in stage T2.

Initial analysis of the cohort revealed that 7-year OS for all patients was approximately 40%. Survival analysis of the entire cohort revealed that the fraction of stained tumor cells positive for anti-RBM3 significantly correlated with OS (FIG. 2), i.e. a high RBM3 protein level corresponded to an improved survival. When the analysis is limited to the subjects having stage T2 cancers, there is a trend towards better survival rates for the subjects showing high levels of RBM3 protein (FIG. 3A). Thus, the data indicate that RBM3 is a stage-independent prognostic factor. When the analysis is limited to subjects having grade 3 cancers, there is also a trend towards better survival rates for the subjects having high levels of RBM3 protein. Thus, the data indicate that RBM3 is also a grade-independent prognostic factor. The reason for the correlations not being significant (i.e. p-values>0.05) is probably that the number of subjects having the respective stage and grade is relatively low (35 subjects in stage T2 and 53 subjects in grade 3).

Cox regression univariate analysis showed that increased RBM3 expression was associated with improved OS(RR=0.54, 95% CI: 0.32-0.91, P=0.02). There was an inverse correlation between RBM3 expression and both T-stage and grade (Spearmans Rho, p<0.001).

3. Epitope Mapping Using Bioplex a) Synthetic Peptide Preparation

A PEPscreen library consisting of 25 biotinylated peptides corresponding to the protein fragment SEQ ID NO:1 of the RBM3 protein (SEQ ID NO:2, SEQ ID NO:3) was synthesized by Sigma-Genosys (Sigma-Aldrich). The peptides were 15 amino acid residues long with a 10 amino acid residues overlap, together covering the entire protein fragment (SEQ ID NO:1). The peptides were resolved in 80% DMSO to a final concentration of 10 mg/ml.

b) Bead Coupling

Neutravidin (Pierce, Rockford, Ill.) was immobilized on carboxylated beads (BioPlex COOH Beads, BioRad) in accordance with the manufacturer's protocol. Coupling of $10^6$ beads was performed using a filter membrane bottomed microtiter plate (MultiScreen-HTS, Millipore, Billerica, Mass.) as previously described (Larsson et al (2009) J Immunol Methods 15; 34(1-2):20-32, Schwenk et al (2007) Mol Cell Proteomics 6(1) 125:32). 25 distinct groups of beads with different color code IDs were activated using 1-Ethyl-3-(3-dimethylamino-propyl) carbodiimide and N-Hydroxysuccinimide. Neutravidin (250 µg/ml in 50 mM Hepes pH 7.4) was added to the beads and incubated for 120 min on a shaker. The beads were finally washed, re-suspended, and transferred to micro-centrifuge tubes for storage at 4° C. in PBS-BN (1×PBS, 1% BSA, 0.05% NaN3). All coupled bead populations were treated with sonication in an ultrasonic cleaner (Branson Ultrasonic Corporation, Danbury, Conn.) for 3 min. The biotinylated peptides were diluted in PBS-BN to a concentration of 0.1 mg/ml, and 50 µl of each peptide was used in the coupling reaction, which was conducted for 60 min with shaking at RT. Finally, the beads were washed with 3×100 µl BRE buffer and stored at 4° C. until further use.

c) Determination of Binding Specificity

A bead mixture containing all 25 bead IDs was prepared and 10 µl of the polyclonal rabbit antibody "anti-RBM3", obtained as described previously (see Examples, section 1 and 2 of WO 2010/092190), was mixed with 30 µl of the bead mix and incubated for 60 min at RT. A filter bottomed microtiter plate (Millipore) was utilized for washing and following each incubation all wells were washed with 2×100 µl PBS-BN. To the beads, 25 µl of R-Phycoerythrine labeled anti-rabbit IgG antibody (Jackson ImmunoResearch) was added for a final incubation of 30 min at RT.

Measurements were performed using the Bioplex 200 Suspension Array instrumentation with Bio-Plex Manager 5.0 software. For each experiment, 50 events per bead ID were counted and the median fluorescence intensity (MFI) was used as a measurement of antibody binding to individual bead populations.

d) Results

The specificities of anti-RBM3 were tested in an assay using beads coupled with synthetic biotinylated peptides. Anti-RBM3 showed strong binding to several of the peptides, among which peptide 6, corresponding to the sequence SEQ ID NO: 20 (a subsequence of SEQ ID NO:1), was one (see FIG. 5).

4. Fractionation of a Polyclonal Anti-RBM3 Antibody a) Materials and Methods

Peptide specific antibodies were obtained by affinity purification of anti-RMB3 against peptides to which the polyclonal anti-RBM3 antibody was shown to bind in Examples, section 3. Among the peptides chosen was peptide 6, and 600 nmol of biotinylated peptide were diluted with HiTrap™ Streptavidin binding buffer to a final volume of 1100 µl and applied to 1 ml HiTrap™ Streptavidin HP columns (GE Healthcare Bio-Sciences AB, Uppsala, Sweden) for binding. After coupling, columns were washed with HiTrap™ Streptavidin binding buffer to remove unbound peptides (and a blank run was performed on all columns prior to sample loading.)

Serum obtained from a New Zeeland white rabbit immunized with the recombinant RBM3 fragment SEQ ID NO: 1 fused to a His$_6$-ABP tag, was purified on a ÄKTAxpress™ (GE Healthcare) liquid chromatography system on eight columns in a serial mode as follows: two 5 ml His$_6$-ABP columns followed by 5 epitope specific peptide columns and at the end a His$_6$-ABP-RBM3 fusion protein column. After sample loading, the columns were washed and eluted in parallel to obtain separate antibody fractions. The eluted antibody fractions were epitope mapped using BioPlex, as described above. To further improve the epitope resolution for the antibody fraction that bound peptide 6, alanine scanning of the peptide was performed using the following method: Twenty biotinylated synthetic peptides of the sequence TQRSRGFGFITFTNPEHASV (SEQ ID NO: 21), each with a single alanine mutation introduced at every residue (Sigma-Aldrich) were dissolved in DMSO and diluted to 4 µmoles peptide in 100 µL PBS 7.4 supplemented with 1 mg/mL BSA. The peptides were coupled to 20 Bioplex neutravidin coated beads with 20 unique reporter dyes as described above. The antibody fraction binding to peptide 6 was incubated for one hour in PBST with a cocktail of the different beads consisting of around 15,000 beads per ID. The antibodies were subsequently labeled with PE-conjugated secondary reagent (Moss Inc., USA) and analyzed using Bioplex 200 Suspension Array instrumentation with Bio-Plex Manager 5.0 software.

b) Results

When the antibody fraction was epitope mapped, the fractionated antibody bound its expected peptide. The antibody fraction that bound to peptide 6 was confirmed to bind the full-length RBM3 protein (SEQ ID NO:2) by IHC and Western Blot analysis. Preserved antibody binding for the fraction that bound peptide 6 was observed for all amino acid positions except the alanine-substitutions Phe12Ala, Thr13Ala, and Asn14Ala of the epitope. The epitope for the antibody fraction was thus determined to include the sequence FTN (SEQ ID NO:22) within SEQ ID NO: 4 (see FIG. 5).

5. Generation of Monoclonal Antibodies a) Materials and Methods

A synthetic peptide (SEQ ID NO: 23), including peptide 6 (SEQ ID NO: 20) and peptide 7 (SEQ ID NO:24) in Section 3 and having a cystein residue added at its N-terminal to which BSA was coupled according to standard procedure, was used as antigen for production of monoclonal antibodies. The antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified. Cell lines that showed positive results in ELISA, Western blot (WB) and immunohistochemistry (IHC) were selected for subcloning.

In addition, the immunohistochemical staining patterns of the monoclonal antibodies were compared to that of anti-RBM3.

b) Results

Cell-lines were screened by ELISA to identify lines that produce monoclonal antibodies (mAbs) that recognize the antigen (SEQ ID NO:1), but not the fusion tag, BSA. There were 37 cell-lines showing specific binding to the antigen SEQ ID NO:1 in ELISA and these were selected for further testing. For each of the selected 37 clones 150-300 µl supernatant was collected and azide was added. The supernatants were stored at +4° C. Further testing of the cell lines showed that clones denoted 7F5, 10F1, 12A10, 12C9, and 14D9 gave positive results in both Western blot and IHC analysis. These clones were selected for subcloning and expansion.

6. Evaluation of Antibody Specificity a) Material and Methods

The specificity of the polyclonal antibody (anti-RBM3), obtained as previously described, and the monoclonal antibodies (7F5, 10F1, 12A10, 12C9, and 14D9), obtained as described in Section 5 above, were analyzed by Western Blot. Western blot was performed by separation of total protein extracts from the human cell line RT4 on 4-20% criterion TGX prep well gels under reducing conditions, followed by electro-transfer to PVDF membranes (Millipore) according to the manufacturer's recommendations. The membranes were blocked (5% milk in 1×TBST (0.1% Tween20)) for 1 h at room temperature, incubated with the primary monoclonal antibody (diluted 1:10 in 1% BSA, 1×TBST) and washed in PBST. The secondary HRP-conjugated antibody (polyclonal goat anti-mouse or polyclonal swine anti-rabbit, both Dako) was diluted 1:3000 in blocking buffer and chemiluminescence detection was carried out using a CCD camera (Syngene) and Immobilon Western Chemiluminescent HRP Substrate (Millipore), according to the manufacturer's protocol.

b) Results

The results of the Western blot analysis shows that the antibodies specifically detect a band of approximately 16 kDa in the RT4 cell line. The theoretical molecular weight of RBM3 is 16 kDa (as calculated from the RBM3 amino acid sequence SEQ ID NO:2), corresponding well to the result obtained. Additional bands were observed for anti- RBM3. Overall, the results show that the monoclonal antibodies were more specific than the polyclonal antibody, (see FIG. 4).

7. Epitope Mapping of Monoclonal Antibodies a) Material and Methods

The monoclonal antibodies obtained as described in Section 5, were epitope mapped using Bioplex. Synthetic peptide preparation and bead coupling was performed as described in Section 3. A bead mixture containing all 25 bead IDs was prepared and 10 µl of the monoclonal antibodies, diluted 1:10 in PBS-BN (1% BSA), was mixed with 5 µl of the bead mix and incubated for 60 min at RT. A filter bottomed microtiter plate (Millipore) was utilized for washing and following each incubation all wells were washed with 3×100 µl PBST. 25 µl of PE-conjugated goat anti-mouse IgG (Jackson ImmunoResearch) were added (4 ug/ml) for a final incubation of 60 min at RT.

Measurements were performed using BioPlex 200 Suspension Array instrumentation with Bio-Plex Manager 5.0 software. For each experiment 50 events per bead ID were counted and the median fluorescence intensity (MFI) was used as a measurement of antibody binding to individual bead populations.

b) Results

The specificities of the monoclonal antibodies were tested in an assay using beads coupled with synthetic biotinylated peptides. All monoclonals tested showed strong binding to 2 of the peptides, namely peptide 7 (SEQ ID NO: 24) and 8, SEQ ID NO: 25 (see FIG. 5) corresponding to the consensus sequence SEQ ID NO: 26 within SEQ ID NO:4.

A Non-Limiting Example of an Establishment of a Prognosis

Following the establishment of a bladder cancer diagnosis in a patient, a tumor tissue sample from the patient is obtained. The tumor tissue sample may be obtained from a biopsy performed earlier during the diagnosis of the cancer or from a specimen from a surgical removal of the tumor. Further, for the provision of a "negative reference", a sample is taken from archival material comprising tissue having low, or essentially lacking, RBM3 protein expression. Such archival tissue may for example be bladder cancer tissue having a pre-established low RBM3 protein expression level. Further, for the provision of a "positive reference", a sample is taken from archival material comprising tissue having high RBM3 protein expression, such as bladder cancer tissue having a pre-established high RBM3 protein expression level.

The sample material is fixated in buffered formalin and histo-processed in order to obtain thin sections (4 µm) of the sample material.

Immunohistochemistry is performed in accordance with the above. One or more sample sections from each sample is/are mounted on glass slides that are incubated for 45 min in 60° C., de-paraffinized (if the sample in question was paraffinized) in xylene (2×15 min) and hydrated in graded alcohols. For antigen retrieval, slides are immersed in TRS (Target Retrieval Solution, pH 6.0, DakoCytomation) and boiled for 4 min at 125° C. in a Decloaking Chamber® (Biocare Medical). Slides are placed in the Autostainer® (DakoCytomation) and endogenous peroxidase is initially blocked with $H_2O_2$ (DakoCytomation). The reason for mounting multiple sample sections is to increase the accuracy of the results.

The monoclonal antibody 1B5 (see above) is added to the slides, which are incubated for 30 min in room temperature, followed by 30 min of incubation in room temperature with a labeled secondary antibody; e.g. goat-anti-peroxidase (rabbit or mouse) conjugated Envision®. To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab) mounting media.

As a tool to validate the staining procedure, two control cell-lines may be used; e.g. one slide with cells expressing RBM3 protein (positive cell line) and one slide having cells with indistinct weak or no RBM3 protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the other slides, i.e. incubated with the same primary and secondary antibodies.

For example, the tumor tissue slides from the subject, the staining reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the stained slides (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the tissue samples is considered invalid and the whole staining procedure is repeated with new slides. If the positive and negative cell-lines display strong staining intensity and indistinct weak or no staining intensity, respectively, the staining is considered as valid.

The stained sample slide(s) from the tumor tissue sample from the patient is/are manually evaluated by visual inspection, and a sample value (NS) of each slide is determined according to the above. The person performing the evaluation and determination is aided by visual inspection of the stained positive and negative reference slides.

The sample value(s) from the tumor tissue sample from the patient is/are then compared to a reference value. If more than one sample slide are evaluated and thereby more than one sample value are obtained, the sample value that is compared to the reference value may be a mean or median value of the obtained sample values.

The reference value may be a NS of 4 In such case it is concluded that the tested patient belongs to a group of patients having a relatively good prognosis if the NF of the sample(s) is higher than 4 and a group of patients having a relatively poor prognosis if the NF of the sample(s) is 4 or lower. The prognoses of the respective groups may be read from dichotomized data as those presented in the figures, wherein the upper curve represents the group of patients having the relatively good prognosis and the lower curve represents the group of patients having the relatively poor prognosis. For example, the relatively good prognosis may be an average five-year overall survival of about 75% and the relatively poor prognosis may be an average five-year overall survival of about 29% (FIG. 1A).

If the cancer of the subject is diagnosed as early stage (i.e. Ta or T1), the respective prognoses may be read from dichotomized data exclusively based on subjects having such early stage cancers, such as in FIG. 1B (good and poor prognosis: about 84% and about 41%, respectively).

All cited material, including but not limited to publications, DNA or protein data entries, and patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. Method of treatment of a subject having a TNM stage T1 bladder cancer with decreased RBM3 expression, comprising the steps of:
    a) evaluating an amount of RBM3 in only the nuclei of tumor cells in at least part of a sample earlier obtained from the subject and determining a sample value corresponding to the evaluated amount;
    b) comparing said sample value with a predetermined reference value based on RBM3 expression levels in the nuclei of tumor cells of subjects having bladder cancer; and
    c) treating said subject with a cystectomy;
wherein said sample value is lower than said reference value.

2. Method of claim 1, wherein step a) comprises:
    aI) applying to said sample a quantifiable affinity ligand capable of selective interaction with the RBM3 protein to be evaluated, said application being performed under conditions that enable binding of the affinity ligand to RBM3 protein present in the sample; and
    aII) quantifying only the affinity ligand bound to the nucleic of tumor cells in said sample to evaluate said amount;
wherein said quantifiable affinity ligand is a monoclonal antibody capable of selective interaction with an RBM3 fragment which consists of 20 amino acid residues or less and comprises a sequence selected from SEQ ID NOS: 8, 16, 17, 22, 24, 25, or 26.

3. Method of claim 1, wherein said subject has not failed to respond to treatment with bacillus Calmette-Guerin.

4. Method of treatment of a subject having a TNM stage T1 bladder cancer with decreased RBM3 expression relative to a predetermined reference value based on RBM3 expression levels in the nuclei of tumor cells of subjects having bladder cancer, comprising treating said subject with a cystectomy.

5. New Method of claim 4, wherein said subject has not failed to respond to treatment with bacillus Calmette-Guerin.

* * * * *

UNITED STATES PATENT AND TRADEMARK OFFICE
CERTIFICATE OF CORRECTION

PATENT NO. : 9,701,741 B2
APPLICATION NO. : 14/117704
DATED : July 11, 2017
INVENTOR(S) : Eberhard et al.

It is certified that error appears in the above-identified patent and that said Letters Patent is hereby corrected as shown below:

On the Title Page

(30) Foreign Application Priority Data: Please correct "11166558" to read -- 11166558.4 --

In the Specification

Column 16, Line 49: Please correct "at least 97 identical," to read -- at least 97% identical, --
    Line 58: Please correct "at least 94° A) identical," to read -- at least 94% identical, --
    Line 59: Please correct "at least 97 identical," to read -- at least 97% identical, --

Column 22, Line 36: Please correct "such as 90 or lower" to read -- such as 90% or lower --

Column 27, Line 46: Please correct "(Fields S and Song 0" to read -- (Fields S and Song O --

In the Claims

Column 54, Claim 5, Line 17: Please correct "New Method of claim 4," to read -- Method of claim 4, --

Signed and Sealed this
Thirty-first Day of July, 2018

Andrei Iancu
*Director of the United States Patent and Trademark Office*

```
                       SEQUENCE LISTING

<160> NUMBER OF SEQ ID NOS: 26

<210> SEQ ID NO 1
<211> LENGTH: 134
<212> TYPE: PRT
<213> ORGANISM: Homo sapiens

<400> SEQUENCE: 1

Asp Glu Gln Ala Leu Glu Asp His Phe Ser Ser Phe Gly Pro Ile Ser
1               5                   10                  15

Glu Val Val Val Lys Asp Arg Glu Thr Gln Arg Ser Arg Gly Phe
            20                  25                  30

Gly Phe Ile Thr Phe Thr Asn Pro Glu His Ala Ser Val Ala Met Arg
            35                  40                  45

Ala Met Asn Gly Glu Ser Leu Asp Gly Arg Gln Ile Arg Val Asp His
    50                  55                  60

Ala Gly Lys Ser Ala Arg Gly Thr Arg Gly Gly Phe Gly Ala His
65                  70                  75                  80

Gly Arg Gly Arg Ser Tyr Ser Arg Gly Gly Gly Asp Gln Gly Tyr Gly
                85                  90                  95

Ser Gly Arg Tyr Tyr Asp Ser Arg Pro Gly Gly Tyr Gly Tyr Gly Tyr
            100                 105                 110

Gly Arg Ser Arg Asp Tyr Asn Gly Arg Asn Gln Gly Gly Tyr Asp Arg
            115                 120                 125

Tyr Ser Gly Gly Asn Tyr
        130

<210> SEQ ID NO 2
<211> LENGTH: 157
<212> TYPE: PRT
<213> ORGANISM: Homo sapiens

<400> SEQUENCE: 2

Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Val Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Gly Phe Gly Ala
                85                  90                  95

His Gly Arg Gly Arg Ser Tyr Ser Arg Gly Gly Gly Asp Gln Gly Tyr
            100                 105                 110

Gly Ser Gly Arg Tyr Tyr Asp Ser Arg Pro Gly Gly Tyr Gly Tyr Gly
            115                 120                 125

Tyr Gly Arg Ser Arg Asp Tyr Asn Gly Arg Asn Gln Gly Gly Tyr Asp
            130                 135                 140
```

Arg Tyr Ser Gly Gly Asn Tyr Arg Asp Asn Tyr Asp Asn
145             150             155

<210> SEQ ID NO 3
<211> LENGTH: 1130
<212> TYPE: DNA
<213> ORGANISM: Homo sapiens

<400> SEQUENCE: 3

```
atgcgcaatg tggcccccta atggtggctg cgctgagcca gctcctcaga ttaccacctt      60
attggccgcc tttctcagct tttctgtagt tacccatatt tgttcctct ttcttgtcta     120
ttttctgtgc ttttctctg ctttccgtct cgctattttc tcacatctcc attttctttc     180
tccttcctgc caccattctt catgttcttc ccacaggact tgaactgcca tgtcctctga     240
agaaggaaag ctcttcgtgg gagggctcaa ctttaacacc gacgagcagg cactggaaga     300
ccacttcagc agtttcggac ctatctctga ggtggtcgtt gtcaaggacc gggagactca     360
gcggtccagg ggttttggtt tcatcacctt caccaaccca gagcatgctt cagttgccat     420
gagagccatg aacggagagt ctctggatgg tcgtcagatc cgtgtggatc atgcaggcaa     480
gtctgctcgg ggaaccagag gaggtggctt tgggggccat gggcgtggtc gcagctactc     540
tagaggtggt ggggaccagg gctatgggag tggcaggtat tatgacagtc gacctggagg     600
gtatggatat ggatatggac gttccagaga ctataatggc agaaaccagg gtggttatga     660
ccgctactca ggaggaaatt acagagacaa ttatgacaac tgaaatgaga catgcacata     720
atatagatac acaaggaata atttctgatc caggatcgtc cttccaaatg gctgtattta     780
taaaggtttt tggagctgca ccgaagcatc ttatttata gtatatcaac cttttgtttt     840
taaattgacc tgccaaggta gctgaagacc ttttagacag ttccatcttt tttttttaaat     900
tttttctgcc tatttaaaga caaattatgg gacgtttgta gaacctgagt attttttcttt     960
ttaccagttt tttagtttga gctcttaggt ttattggagc tagcaataat tggttctggc    1020
aagtttggcc agactgactt caaaaaatta atgtgtatcc agggacattt taaaaacctg    1080
tacacagtgt ttattgtggt taggaagcaa tttcccaatg tacctataag                1130
```

<210> SEQ ID NO 4
<211> LENGTH: 29
<212> TYPE: PRT
<213> ORGANISM: Homo sapiens

<400> SEQUENCE: 4

Arg Gly Phe Gly Phe Ile Thr Phe Thr Asn Pro Glu His Ala Ser Val
1               5                   10                  15

Ala Met Arg Ala Met Asn Gly Glu Ser Leu Asp Gly Arg
            20                  25

<210> SEQ ID NO 5
<211> LENGTH: 24
<212> TYPE: PRT
<213> ORGANISM: Homo sapiens

<400> SEQUENCE: 5

Arg Ser Tyr Ser Arg Gly Gly Gly Asp Gln Gly Tyr Gly Ser Gly Arg
1               5                   10                  15

Tyr Tyr Asp Ser Arg Pro Gly Gly
            20

<210> SEQ ID NO 6

```
<211> LENGTH: 5
<212> TYPE: PRT
<213> ORGANISM: Homo sapiens

<400> SEQUENCE: 6

Thr Phe Thr Asn Pro
1               5

<210> SEQ ID NO 7
<211> LENGTH: 10
<212> TYPE: PRT
<213> ORGANISM: Homo sapiens

<400> SEQUENCE: 7

Gly Thr Arg Gly Gly Gly Phe Gly Ala His
1               5                   10

<210> SEQ ID NO 8
<211> LENGTH: 10
<212> TYPE: PRT
<213> ORGANISM: Homo sapiens

<400> SEQUENCE: 8

Gly Phe Gly Ala His Gly Arg Gly Arg Ser
1               5                   10

<210> SEQ ID NO 9
<211> LENGTH: 5
<212> TYPE: PRT
<213> ORGANISM: Homo sapiens

<400> SEQUENCE: 9

Tyr Asp Arg Tyr Ser
1               5

<210> SEQ ID NO 10
<211> LENGTH: 9
<212> TYPE: PRT
<213> ORGANISM: Homo sapiens

<400> SEQUENCE: 10

Asp Glu Gln Ala Leu Glu Asp His Phe
1               5

<210> SEQ ID NO 11
<211> LENGTH: 7
<212> TYPE: PRT
<213> ORGANISM: Homo sapiens

<400> SEQUENCE: 11

Thr Asn Pro Glu His Ala Ser
1               5

<210> SEQ ID NO 12
<211> LENGTH: 10
<212> TYPE: PRT
<213> ORGANISM: Homo sapiens

<400> SEQUENCE: 12

Glu His Ala Ser Val Ala Met Arg Ala Met
1               5                   10

<210> SEQ ID NO 13
<211> LENGTH: 10
<212> TYPE: PRT
```

-continued

<213> ORGANISM: Homo sapiens

<400> SEQUENCE: 13

Arg Gly Gly Gly Phe Gly Ala His Gly Arg
1               5                   10

<210> SEQ ID NO 14
<211> LENGTH: 8
<212> TYPE: PRT
<213> ORGANISM: Homo sapiens

<400> SEQUENCE: 14

Gly Phe Gly Ala His Gly Arg Gly
1               5

<210> SEQ ID NO 15
<211> LENGTH: 9
<212> TYPE: PRT
<213> ORGANISM: Homo sapiens

<400> SEQUENCE: 15

Asp Tyr Asn Gly Arg Asn Gln Gly Gly
1               5

<210> SEQ ID NO 16
<211> LENGTH: 10
<212> TYPE: PRT
<213> ORGANISM: Homo sapiens

<400> SEQUENCE: 16

His Gly Arg Gly Arg Ser Tyr Ser Arg Gly
1               5                   10

<210> SEQ ID NO 17
<211> LENGTH: 7
<212> TYPE: PRT
<213> ORGANISM: Homo sapiens

<400> SEQUENCE: 17

Gly Ser Gly Arg Tyr Tyr Asp
1               5

<210> SEQ ID NO 18
<211> LENGTH: 6
<212> TYPE: PRT
<213> ORGANISM: Homo sapiens

<400> SEQUENCE: 18

Ser Gly Arg Tyr Tyr Asp
1               5

<210> SEQ ID NO 19
<211> LENGTH: 3
<212> TYPE: PRT
<213> ORGANISM: Homo sapiens

<400> SEQUENCE: 19

Asp Glu Gln
1

<210> SEQ ID NO 20
<211> LENGTH: 15
<212> TYPE: PRT
<213> ORGANISM: Homo sapiens

```
<400> SEQUENCE: 20

Thr Gln Arg Ser Arg Gly Phe Gly Phe Ile Thr Phe Thr Asn Pro
1               5                   10                  15

<210> SEQ ID NO 21
<211> LENGTH: 20
<212> TYPE: PRT
<213> ORGANISM: Homo sapiens

<400> SEQUENCE: 21

Thr Gln Arg Ser Arg Gly Phe Gly Phe Ile Thr Phe Thr Asn Pro Glu
1               5                   10                  15

His Ala Ser Val
            20

<210> SEQ ID NO 22
<211> LENGTH: 3
<212> TYPE: PRT
<213> ORGANISM: Homo sapiens

<400> SEQUENCE: 22

Phe Thr Asn
1

<210> SEQ ID NO 23
<211> LENGTH: 21
<212> TYPE: PRT
<213> ORGANISM: Homo sapiens

<400> SEQUENCE: 23

Cys Thr Gln Arg Ser Arg Gly Phe Gly Phe Ile Thr Phe Thr Asn Pro
1               5                   10                  15

Glu His Ala Ser Val
            20

<210> SEQ ID NO 24
<211> LENGTH: 15
<212> TYPE: PRT
<213> ORGANISM: Homo sapiens

<400> SEQUENCE: 24

Gly Phe Gly Phe Ile Thr Phe Thr Asn Pro Glu His Ala Ser Val
1               5                   10                  15

<210> SEQ ID NO 25
<211> LENGTH: 15
<212> TYPE: PRT
<213> ORGANISM: Homo sapiens

<400> SEQUENCE: 25

Thr Phe Thr Asn Pro Glu His Ala Ser Val Ala Met Arg Ala Met
1               5                   10                  15

<210> SEQ ID NO 26
<211> LENGTH: 10
<212> TYPE: PRT
<213> ORGANISM: Homo sapiens

<400> SEQUENCE: 26

Thr Phe Thr Asn Pro Glu His Ala Ser Val
1               5                   10
```